United States Patent
Riis et al.

(10) Patent No.: US 10,639,474 B2
(45) Date of Patent: May 5, 2020

(54) HEARING AID SYSTEM AND A METHOD OF OPERATING THEREOF

(71) Applicants: Oticon Medical A/S, Smørum (DK); University College London, London (GB)

(72) Inventors: Søren Kamaric Riis, Smørum (DK); Attila Frater, London (GB); Torsten Marquardt, London (GB)

(73) Assignees: OTICON MEDICAL A/S, Smørum (DK); UNIVERSITY COLLEGE LONDON, London (GB)

( * ) Notice: Subject to any disclaimer, the term of this patent is extended or adjusted under 35 U.S.C. 154(b) by 384 days.

(21) Appl. No.: 15/592,901

(22) Filed: May 11, 2017

(65) Prior Publication Data

US 2017/0326366 A1 Nov. 16, 2017

(30) Foreign Application Priority Data

May 12, 2016 (EP) .................................. 16169397

(51) Int. Cl.
*A61N 1/00* (2006.01)
*A61N 1/36* (2006.01)
(Continued)

(52) U.S. Cl.
CPC ....... *A61N 1/36038* (2017.08); *A61N 1/0541* (2013.01); *A61N 1/36036* (2017.08);
(Continued)

(58) Field of Classification Search
CPC ............ A61N 1/36038; A61N 1/36036; A61N 1/0541; H04R 25/353; H04R 25/356;
(Continued)

(56) References Cited

U.S. PATENT DOCUMENTS

2005/0261748 A1  11/2005  van Dijk
2012/0059438 A1   3/2012  De Ridder
(Continued)

FOREIGN PATENT DOCUMENTS

WO  WO 2015/018457 A1  2/2015

*Primary Examiner* — Mallika D Fairchild
(74) *Attorney, Agent, or Firm* — Birch, Stewart, Kolasch & Birch, LLP

(57) ABSTRACT

According to an embodiment, a hearing aid system is disclosed. The system includes a speech processor communicatively coupled to a microphone. The speech processor is configured to process a microphone signal received at the speech processor for producing an electrical stimulation signal and an acoustic stimulation signal. The speech processor is also configured to generate a modified acoustic stimulation signal by modifying the acoustic stimulation signal at least for a part of a residual frequency range of a patient in dependence on effect of an implantable electrode array on mechanical properties of cochlea of the patient. The system also includes a first unit and a second unit. The first unit comprising a cochlear implant communicatively coupled to the speech processor, the cochlear implant comprising the implantable electrode array configured to be located within a cochlea of the patient and to provide the electrical stimulation based on the electrical stimulation signal to a cochlea within a non-residual frequency range of the patient. The second unit communicatively coupled to the speech processor and adapted to provide the modified acoustic stimulation based on the modified acoustic stimulation signal to the cochlea within the at least in the part of the residual frequency range.

17 Claims, 8 Drawing Sheets

(51) Int. Cl.
*H04R 25/00* (2006.01)
*A61N 1/05* (2006.01)

(52) U.S. Cl.
CPC ........... *H04R 25/35* (2013.01); *H04R 25/353* (2013.01); *H04R 25/356* (2013.01); *H04R 25/505* (2013.01); *H04R 25/70* (2013.01); *H04R 25/554* (2013.01); *H04R 2225/021* (2013.01); *H04R 2225/43* (2013.01); *H04R 2225/55* (2013.01); *H04R 2225/67* (2013.01); *H04R 2460/13* (2013.01)

(58) Field of Classification Search
CPC ...... H04R 25/505; H04R 25/70; H04R 25/35; H04R 25/50; H04R 2225/43; H04R 2225/67; H04R 2225/021; H04R 2225/55; H04R 2460/13
See application file for complete search history.

(56) References Cited

U.S. PATENT DOCUMENTS

| | | | |
|---|---|---|---|
| 2014/0275730 A1* | 9/2014 | Lievens | H04R 25/606 600/25 |
| 2015/0289787 A1 | 10/2015 | Buchman et al. | |
| 2015/0334495 A1 | 11/2015 | Menzl et al. | |
| 2016/0175591 A1* | 6/2016 | Chalupper | A61B 5/16 607/3 |

* cited by examiner

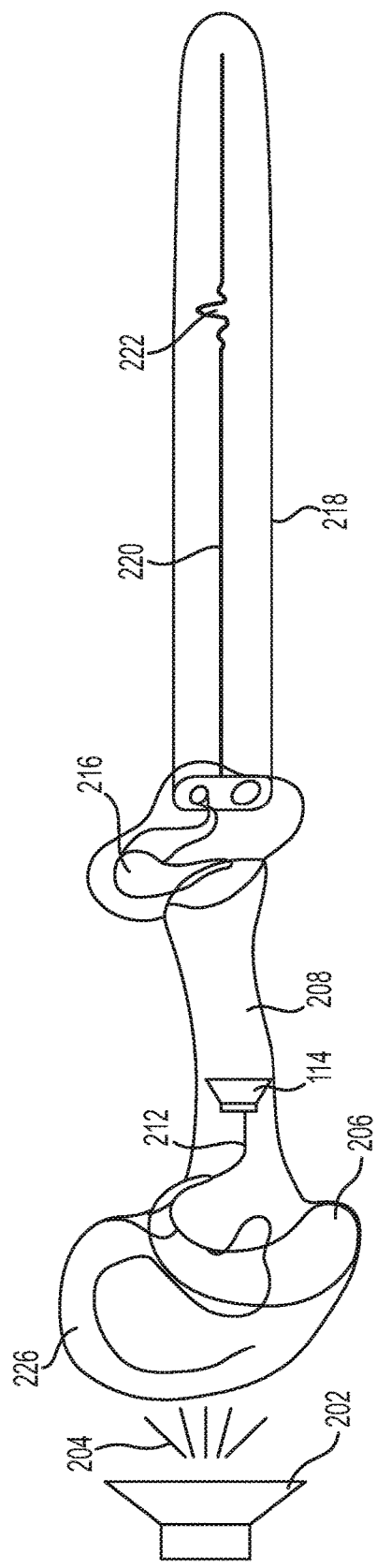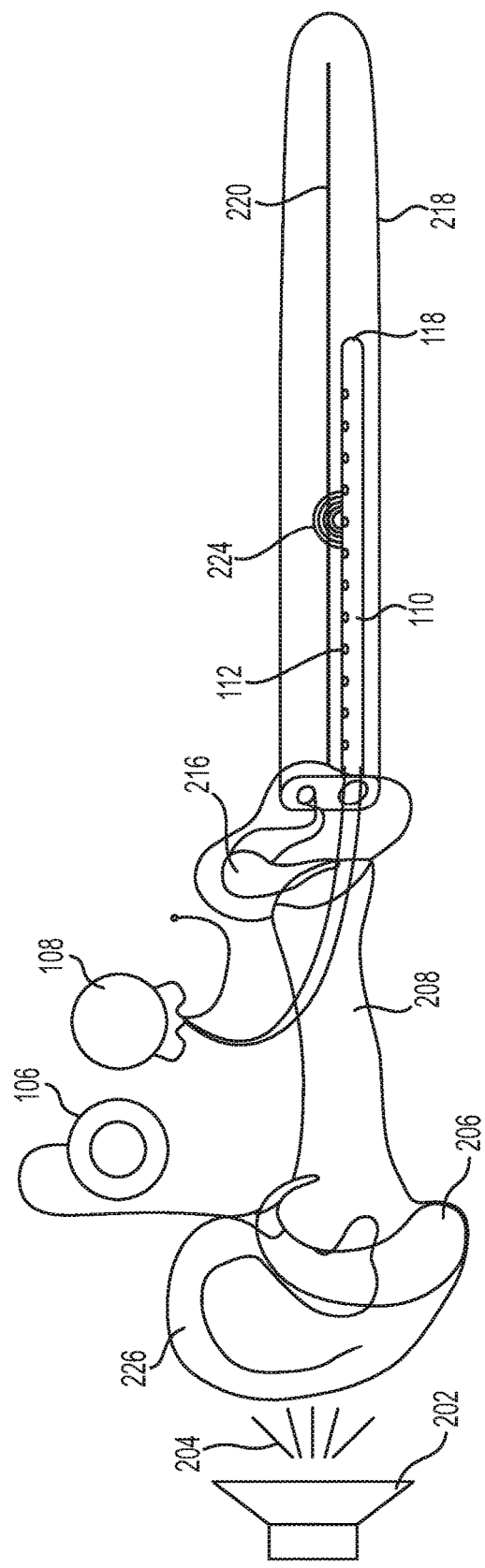

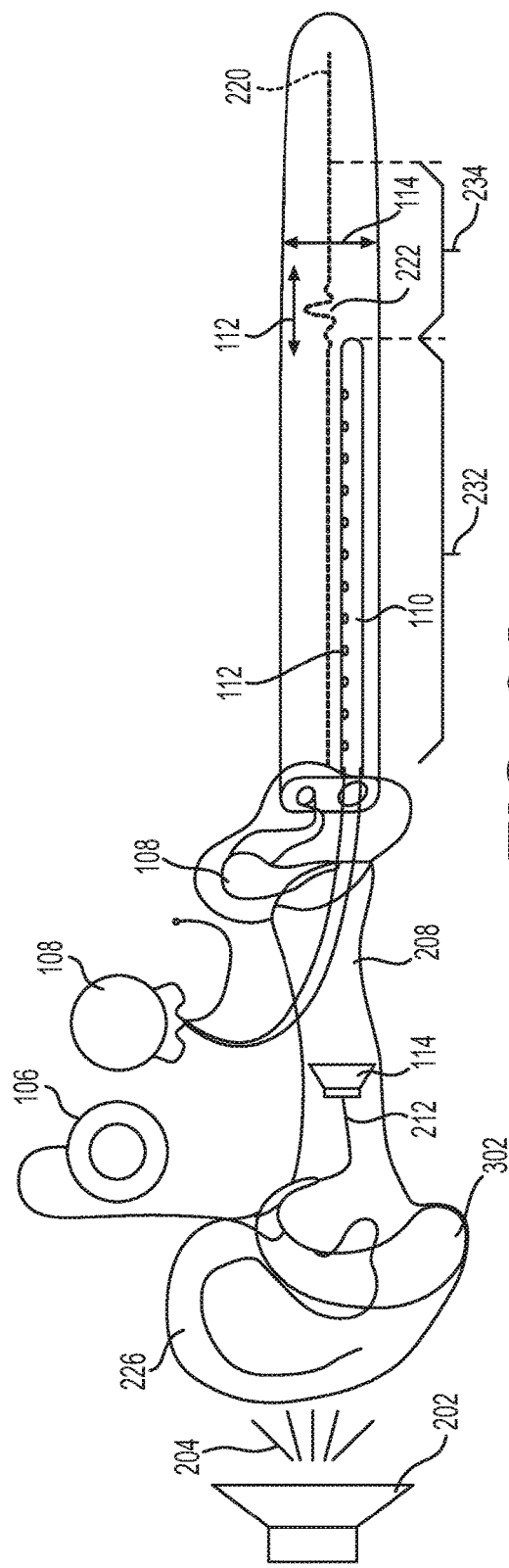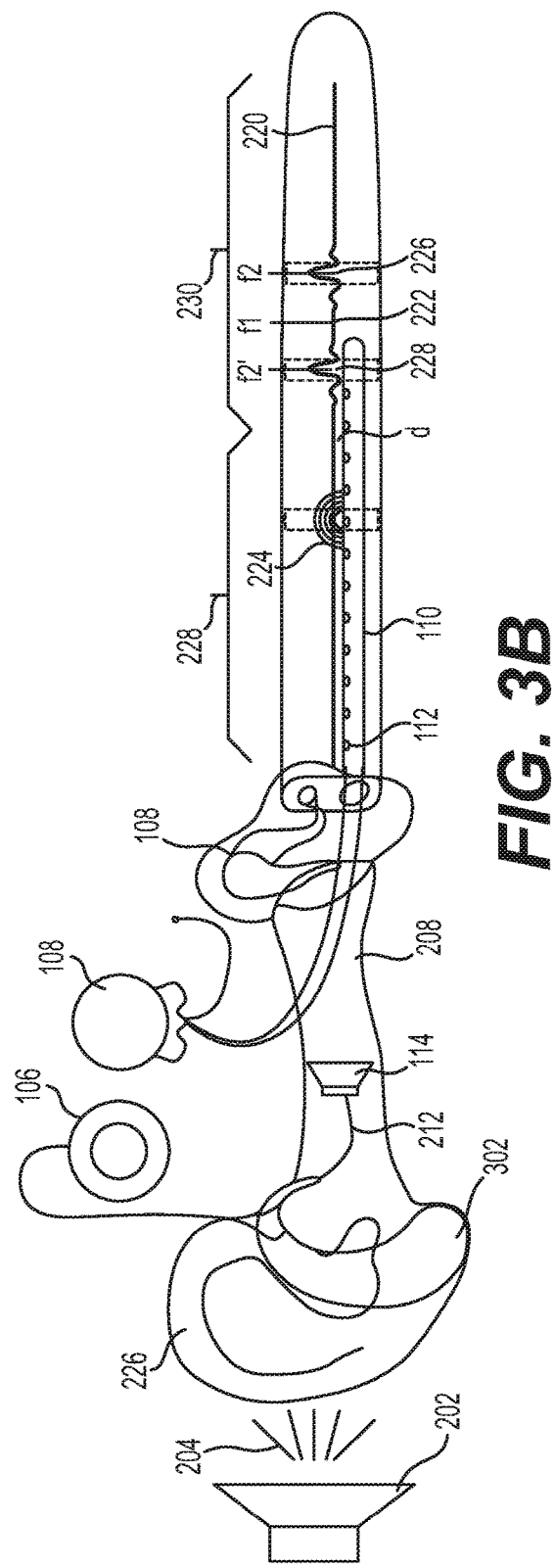

HEARING AID SYSTEM AND A METHOD OF OPERATING THEREOF

FIELD

The present disclosure relates to stimulating an ear of a user of a hearing aid system utilizing different stimulation modes. In particular, the disclosure relates to hearing aid system comprising a first unit such as a cochlear implant and a second unit such as an acoustic hearing aid or a bone conduction hearing aid. The first unit and the second unit are adapted to stimulate same cochlea of the hearing aid user. The disclosure also relates to a method of operating the hearing aid system.

BACKGROUND

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the cochlea are impeded. These sound pathways may be impeded, for example, by damage to the ossicular chain, excessive cerumen, or a malformed Tympanic Membrane. Conductive hearing losses may be treated with acoustic hearing aids, or a bone conduction hearing aid.

Sensorineural hearing loss, on the other hand, is primarily caused by the absence or destruction of the hair cells on the basilar membrane. To overcome sensorineural hearing loss, numerous cochlear implant systems—or cochlear prostheses—have been developed. Cochlear implant systems bypass the major part of the ear by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function. Cochlear implants are typically capable of providing information in higher frequencies such as up to 8 kHz or even higher.

There is a group of people that has some degree of residual hearing, which may also include moderate to severe hearing loss, typically in the low frequencies (e.g., below 1 kHz) and a severe-to-profound hearing loss usually in the high frequencies (e.g., above 1 kHz). However, this group may also include people who retain residual hearing in non-contiguous frequency ranges such as below 1 KHz but also between 2 and 3 kHz and so on.

These people having residual hearing cannot benefit from traditional amplification because of the severity of the hearing loss generally in the high frequencies. Nor are they classic cochlear implant candidates, because of their mostly intact residual hearing.

For this group of people, various dual-mode stimulators such as electro-acoustic stimulation ("EAS") systems have been developed that provide such patients with the ability to perceive sound both in frequency ranges where residual hearing is retained, i.e. residual frequency range and frequency ranges where residual hearing is absent, i.e. non residual frequency range. Electro-acoustic stimulation refers to the use of an acoustic hearing aid and a cochlear implant together in the same ear. The acoustic hearing aid acoustically amplifies the signal in residual frequency range, i.e. frequencies where residual hearing is retained typically in low frequencies, while the cochlear implant electrically stimulates in the non-residual frequency range, i.e. frequencies where residual hearing is not retained or absent typically because of loss or destruction of hair cells. The auditory nerve combines the acoustic and electric stimuli to one auditory signal. Results of various studies have shown a highly synergistic effect between hearing aid and cochlear implant technology, particularly evident in speech understanding, pitch discrimination, and music appreciation.

However, electro-acoustic stimulation systems suffer in performance because the perceptual sensitivity of a patient to acoustic stimulation is quite different in absence of electrical stimulation vis-a-vis when electrical stimulation by way of cochlear implant comprising an implantable electrode array is present in cochlea of the patient. Unfortunately, currently available solutions do not address this issue effectively, thereby making it difficult for a patient to adjust to such dual-mode stimulation and a patient unknowingly suffers from sub-optimal EAS system performance. Some solutions recommend partial insertion or short electrodes in order to avoid effects on cochlear mechanics in the residual frequency range. However, this has a significant drawback that electrical stimulation in the residual frequency range is not possible if a part of the residual hearing is lost, that is residual frequency range is narrowed for reasons such as consequence of the cochlear implant surgery or over time due to aging.

There exists a need to offer an alternative to currently available solutions.

SUMMARY

According to an embodiment, a hearing aid system is disclosed. The system includes a speech processor communicatively coupled to a microphone. The speech processor is configured to process a microphone signal received at the speech processor for producing an electrical stimulation signal and an acoustic stimulation signal. The speech processor is also configured to generate a modified acoustic stimulation signal by modifying the acoustic stimulation signal at least for a part of a residual frequency range of a patient in dependence on effect of an implantable electrode array on mechanical properties of cochlea of the patient. The system also includes a first unit and a second unit. The first unit comprising a cochlear implant communicatively coupled to the speech processor, the cochlear implant comprising the implantable electrode array configured to be located within a cochlea of the patient and to provide the electrical stimulation based on the electrical stimulation signal to a cochlea within a non-residual frequency range of the patient. The second unit communicatively coupled to the speech processor and adapted to provide the modified acoustic stimulation based on the modified acoustic stimulation signal to the cochlea within the at least in the part of the residual frequency range.

Generally, residual hearing refers to the ability of a patient to hear some sounds even if a hearing loss exists. This may not necessarily mean that the patient hearing threshold in the residual frequency range is same as a normal hearing person across the same frequency range. In other words, the phrase "residual hearing" refers to capability of the patient to hear sound when a frequency specific amplitude of stimulation signal is above the threshold of the patient. Residual frequency range thus refers to frequencies where residual hearing is retained typically in low frequencies such as below 1 kHz. However, residual hearing may also be retained in non-contiguous frequency ranges such as below 1 KHz but also between 2 and 3 kHz and so on. Therefore, the residual frequency range also refers to scenarios of such non-contiguous frequency ranges. Non-residual frequency range refers to frequencies where residual hearing is not retained/absent. This may be for reasons such as loss or destruction of hair cells. Non-residual frequency range typically exists over 1 kHz but in view of retention of the residual hearing in the non-contiguous frequency ranges, the non-residual frequency range may also include discontinuous frequency ranges. For example, for residual frequency range that includes below 1 kHz and 2 to 3 kHz, the non-residual range would include 1 to 2 kHz and 3 to 8 kHz and so on. In this scenario, the speech processor is configured to provide acoustic stimulation below 1 kHz and 2 to 3 kHz and electrical stimulation from 1 kHz to 2 kHz and above 3 kHz. However, in scenarios where a continuous residual and non-residual frequency ranges exist such as below 1 kHz defining residual frequency range and above and including 1 kHz defining the non-residual frequency range, a cut-off frequency of 1 kHz may be defined and the speech processor is configured to provide acoustic stimulation using the second unit for frequency below 1 kHz and electrical stimulation above 1 kHz using the first unit. In either scenarios, band pass filters of a filterbank may be utilized for dividing microphone signals into frequency bands (i.e. band limited microphone signals) corresponding to the residual frequency range and non-residual frequency range. Thus, the speech processor is configured to process band limited microphone signals to produce frequency band specific acoustic stimulation signal and/or electrical stimulation signal depending upon whether the frequency band lies within the residual frequency range or non-residual frequency range respectively.

Residual frequency range for the patient may be determined with conventionally known technique such as by measuring neural response to acoustic and/or electrical stimulations, and/or by means of standard audiometric measurement procedures [e.g. Arlinger, S. (1991), *Manual of Practical Audiometry—Volume 2, London*: Whurr Publishers Ltd.]. These standard audiometric measurement procedures may also include Auditory Brainstem Response (ABR) and Electrical Auditory Brainstem Response (eABR) assessments.

The hearing aid system employs a dual stimulation mechanism of the electrical stimulation and acoustic stimulation. In the electrical stimulation pathway, the speech processor processes an external sound captured by the microphone and converts the captured sound into a cochlear processed signal. The speech processor sends the processed signal corresponding to non-residual frequency range to the implant. The implant converts the received processed signal into electrical energy and sends the electrical energy to an electrode array that is positioned inside the cochlea. In the acoustic stimulation pathway, the speech processor processes the external sound captured by the microphone and coverts the captured sound into a processed signal comprising an amplified gain in the residual frequency range. This processed signal comprising the amplified gain is then sent to the cochlea by way of a loudspeaker following the normal hearing pathway based on air conduction principle or by way of a bone conduction hearing aid utilizing a vibrator and bone conduction principle. The amplified processed signal activate the hearing nerves in the residual frequency range. The nerve hearing response caused by the electrical stimulation and acoustic stimulation is sent to the brain, which combines them into a perceived sound.

In an embodiment, the second unit is selected from a group consisting of an acoustic hearing aid configured to provide an air conduction acoustic simulation and a bone conduction hearing aid configured to provide a bone conduction acoustic stimulation.

In one embodiment, the speech processor is configured to be an external speech processor and configured to be positioned external to the patient. The speech processor may be configured to utilize an external transmitter coil to transmit the cochlear processed signal to a receiver coil implantable subcutaneously under the patient skin. The transmitter coil and the receiver coil may include a first magnet and a second magnet respectively, wherein the first magnet and the second magnet are attractable towards each other, thus allowing the external coil to be positioned and aligned with the receiver coil. The receiver coil is configured to communicate with an implantable stimulator unit of the cochlear implant such that the stimulator unit delivers the electrical energy corresponding to the received cochlear processed signal to electrodes of the implantable electrode array that is positioned within cochlea of the patient. In case an acoustic hearing aid is used for providing air conduction acoustic stimulation, the speech processor is electrically coupled to a speaker, which produces an amplified sound in accordance with the amplified processed signal. However, in case a bone conduction hearing aid is used for providing bone conduction acoustic stimulation, the speech processor is communicatively coupled to a vibrator of the bone conduction hearing aid, thus producing a vibration corresponding to the amplified processed signal, the vibrations being transmitted to the cochlea through skull bone. The vibrator may include an external vibrator or an implantable vibrator. In the former scenario, the external speech processor may be electrically coupled to the vibrator through wired means or through an inductive link comprising the external transmitter coil and an external receiver coil of the bone conduction hearing aid, whereas in the latter scenario, an inductive link between the external transmitter coil of the external speech processor and the internal receiver coil of the implantable vibrator allows the implantable vibrator to receive the amplified processed signal.

In another embodiment, the speech processor may be an internal speech processor and configured to be implanted subcutaneously under the patient skin. The speech processor may be communicatively coupled to the implantable stimulator in a wired or wireless (such as by inductive link) arrangement. The implantable stimulator unit of the cochlear implant delivers the electrical energy corresponding to the received cochlear processed signal to electrodes of the implantable electrode array that is positioned within the cochlea. In case of acoustic stimulation using an air conduction stimulation, the speech processor may transmit acoustic processed signal to the acoustic hearing aid by way of an inductive link whereby an internal transmitter coil of an implantable speech processor transmits the amplified processed signal to an external receiver coil that provides the amplified processed signal to the speaker, which produces an amplified sound in accordance with the amplified processed signal. However, in case a bone conduction hearing aid is used for providing bone conduction acoustic stimulation, the speech processor is communicatively coupled to a vibrator of the bone conduction hearing aid, thus producing a vibration corresponding to the amplified processed signal and the vibrations being delivered to the cochlea through skull bone. The vibrator may include an external vibrator or an implantable vibrator. In the former scenario, an inductive link between the internal transmitter coil of the internal speech processor and the external receiver coil of the bone conduction hearing aid allows the implantable vibrator to receive the amplified processed signal whereas in the latter scenario, the speech processor may be electrically coupled to the vibrator through wired means or through implantable inductive link comprising implantable transmitter coil of the speech processor and an implantable receiver coil of the bone conduction hearing aid.

In one embodiment, the acoustic hearing aid may include a tube leading air-borne acoustic signals from an external speech processor into ear canal. In another embodiment, the acoustic hearing aid may include communicative coupling between the speech processor and a speaker arranged close to or in the cartilaginous region of the ear canal, or in the pinna, or in the bony region of the ear canal.

In one embodiment, the speech processor unit is positionable as a Behind-the-Ear type, i.e. the speech processor unit is held on the pinna of the patient or positionable over the receiver coil using the attractive force between the first magnet of the transmitter coil and the second magnet of the receiver coil. In another embodiment, the implantable speech processor unit is positioned subcutaneously under patient's skin.

In one embodiment, the bone conduction hearing aid is a percutaneous bone anchored hearing aid such that the vibrator is mounted on the skull bone using conventionally known screw-fixture mechanism. In another embodiment, the bone conduction hearing aid a direct drive transcutaneous bone conduction hearing aid comprising an implantable vibrator. The term "direct drive" means that vibrations from the vibrator are transferred directly to the skull bone. In another embodiment, the bone conduction hearing aid is a passive drive transcutaneous bone conduction hearing aid comprising an external vibrator. The term "passive drive" means that the vibrations from the vibrator are transferred indirectly such as through the skin to the skull bone.

In an embodiment, the implantable speech processor unit comprises a microphone, a filter bank and the speech processor. In another embodiment, the speech processor unit comprises an external speech processor unit comprising a microphone, a filter bank and a speech processor. In another embodiment, an implantable speech processor unit includes a filter bank, and a speech processor whereas the microphone is an external microphone. The external microphone may be placed at the ear or in the vicinity such as behind the ear, in the ear or canal, etc.

In an embodiment, the microphone is configured to receive a sound such as from environment or other audio sources and generate a microphone signal. In an embodiment, the microphone may include a microphone array, e.g. for providing direction-dependent audio signal processing in different beamforming modes. Beamforming involves processing audio signals received at the microphones of the array in such a way as to make the array act as a highly directional microphone.

In an embodiment, the filter bank is communicatively coupled to the microphone. The filter bank includes an array of frequency specific signal filters that separates the microphone signal into a plurality of band limited microphone signals. Typically, the filter bank has a number of narrow frequency band filters with each filter associated with a specific band of audio frequencies. The microphone signal is thus filtered into the plurality of band limited microphone signals where each signal corresponds to the band of frequencies for one of the band pass filters. The narrow frequency band filters of the filter band is configured such that one or more band limited microphone signals within the residual frequency range are non-overlapping with one or more than one band limited microphone signals within non-residual frequency range. For generating the acoustic stimulation signal and/or electrical stimulation signal, the speech processor is configured to process at least one of these band limited microphone signals in accordance with the frequency range of the band limited microphone signals, i.e. whether the band limited microphone signal is within the residual frequency range or non-residual frequency range, and accordingly generate at least one of the acoustic stimulation signal and electrical stimulation signal.

In an embodiment, the speech processor is communicatively coupled to the filterbank and configured to process the one or more than one band limited microphone signals within the residual frequency range in accordance with an audiogram of the patient. Typically, the audiogram of the patient determines amplification (first gain) specific to a frequency (first frequency) that needs to be applied on frequency specific band limited microphone signal such that the amplified microphone signal (representing the acoustic stimulation signal) is perceived by the patient at least substantially at the same loudness and/or speech intelligibility as a listener having normal hearing when the second unit is used to apply the acoustic stimulation signal.

Cochlea is a finely tuned biomechanical structure that spatially separates the frequency content of the signals. The acoustic energy enters the cochlear via the oval window and initiates a travelling wave that extends along the basilar membrane. For each frequency content, the travelling wave builds up a maximum at a designated place along the basilar membrane which corresponds to the characteristic frequency of that location. This is determined by the stiffness and the effective mass of the vibrating structure, such as basilar membrane. In addition, a process that is mediated by the outer hair cells is initiated. This cochlear mechanical process serves to amplify the peak of the wave at the characteristic frequency location. For a hearing aid system that is configured to provide both electrical stimulation and acoustic stimulation, an introduction of the implantable electrode in the cochlea of the patient may alter mechanical properties of the cochlea such as stiffness of basilar membrane, thus affecting perception of acoustic stimuli. Therefore, providing acoustic stimulation having the first gain at the first frequency within the residual frequency range offers a sub-optimal acoustic stimulation. Accordingly, in an embodiment, the speech processor is configured to produce a modified acoustic stimulation signal by modifying the acoustic stimulation signal at least for a part of a residual frequency range of the patient in dependence on effect of an implantable electrode array on mechanical properties of cochlea of the patient. By way of this modification, the speech processor allows for retaining audiogram based loudness perception and/or speech intelligibility within the residual frequency range despite change in mechanical properties of the cochlea because of the introduction of the electrode array in the cochlea.

In an embodiment, the speech processor is configured to generate the acoustic stimulation signal comprising a first gain corresponding to a first frequency comprised within the residual frequency range in accordance with an audiogram of the patient. The speech processor is further configured to modify at least one of the first gain and the first frequency to generate the modified acoustic stimulation signal comprising at least one of a second gain at the first frequency, the first gain at a second frequency and the second gain at the second frequency. The modification allows for counteracting the effect of the implantable electrode array on mechanical properties of the cochlea Typically, the second gain is higher than the first gain and second frequency is lower than the first frequency. Thus, in an embodiment, where the change in mechanical properties of the cochlea due to presence of implantable electrode array in cochlea results in generally reduced gain and a frequency deviation to a higher resonance frequency vis-a-vis patient's audiogram based frequency specific gain; then generating at least one of the second gain and the second frequency during signal processing counters the reduction and the effect of the change in mechanical properties. The modified acoustic stimulation may thus include a compensatory higher gain (second gain) at a lower frequency (second frequency). Therefore, the effect of change in mechanical properties of the cochlea on the second gain at the second frequency with implantable electrode array in position would effectively produce the first gain at the first frequency. In other words, application of the modified acoustic stimulation with electrode array in position within the cochlea would simulate a scenario through signal processing that reflects acoustic stimulation using the acoustic stimulation signal where the effect of the implanted electrode array is counteracted, thus offering a tonotopically corrected acoustic stimulation and an optimal dual stimulation performance such as in Electroacoustic simulators.

In an embodiment, the effect of the electrode array on mechanical properties of cochlea comprises change in integrity of fine structures in the cochlea clue to presence of the electrode array in the cochlea, thereby affecting the mechano-electric transduction characteristics of the cochlea at least in the part of the residual frequency range. The fine structures may include at least one of basilar membrane, osseous spiral lamina, and spiral ligament. In an embodiment, the effect of the electrode array on mechanical properties of cochlea comprises an increase in stiffness of at least a part of basilar membrane of the cochlea due to presence of the electrode array in the cochlea. In one embodiment, the increase in stiffness is along a length of basilar membrane that is adjacent to the electrode array. This may be because of at least one of the close contact of the electrode array with the basilar membrane at least in some distinct section of the basilar membrane such as at middle turns of the cochlea. In another embodiment, the increase in stiffness of basilar membrane is along a first length of basilar membrane that is adjacent to the electrode array and a second length of the basilar membrane that extends a distance beyond the first length. The second length is continuous to the first length and extends beyond a tip of the electrode array until a certain distance away from the tip. In these embodiments, the increase in stiffness along the first length and/or second length is dependent upon characteristics of the implantable electrode array. These characteristics may include one or a combination of a design of the implantable electrode array, mechanical properties of the implantable electrode array, insertion length of the implantable electrode array, distance of the implantable electrode array from the basilar membrane when the electrode array is located within the cochlea, and insertion technique for locating implantable electrode array into the cochlea. For example, the design of the electrode array may include whether the electrode array has modiolus-hugging capability, or whether the electrode array is straight. In position within the cochlea, the distance between modiolus hugging electrode array and the basilar membrane is smaller than that between the basilar membrane and the straight electrode, which are usually located at the outer circumference of the scala tympani. The mechanical properties may include at least one of the thickness of the electrode array, length of the electrode array, uniform or varying lengthwise stiffness of the electrode array. The thickness of the electrode array may include a uniform thickness electrode array or a varying thickness electrode array comprising a thickness reducing from basal end of the electrode to the tip of the electrode array, the basal end of the end being proximal to base of the cochlea in implanted position. The stiffness of the varying thickness electrode array typically reduces along the length of the electrode array from the basal end to the tip.

A combination of characteristics of electrode array would usually determine increase in stiffness of the basilar membrane. For example, a modiolus hugging curved and stiffer material electrode array would stiffen up the basilar membrane more than a straight design thinner electrode array. Therefore, for a patient, the modification values (amplitude shift and/or frequency shift) required to generate the modified acoustic stimulation for the implantable modiolus hugging stiffer material electrode array will be higher than a straight design relatively flexible electrode array. The skilled person would appreciate that such stiffening of the basilar membrane typically adjacent to the electrode is caused by mechanical pressure of the electrode against the basilar and may also include contact of the electrode array with the basilar membrane. In an embodiment, the insertion technique may include insertion depth of the electrode array in the cochlea when the electrode array is in implanted position. This may further include route of access such as cochleostomy versus round window.

In an embodiment, the speech processor is configured to access a conversion model stored in a memory to generate the modified acoustic stimulation signal. As indicated previously, the modified acoustic stimulation signal is configured to at least substantially counter the effect of the implantable electrode array on mechanical properties of the cochlea of the patient. In an embodiment, the memory may be part of speech processor unit. In another embodiment, the speech processor unit may be configured to access a remote memory separate from the speech processor unit through a wireless link such as Bluetooth for example accessing memory of a communicatively coupled smartphone.

In an embodiment, the conversion model comprises a conversion function comprising at least one of an amplitude shift from the first gain to the second gain and a frequency shift from the first frequency to the second frequency for at least substantially countering the effect of the implantable electrode array on mechanical properties of the cochlea of the patient. Usually, the amplitude shift and/or the frequency shift is proportional to an increase in stiffness of the basilar membrane region corresponding to the first frequency due to the introduction of the electrode array.

In an embodiment, the conversion function includes an outcome of a simulation model. The simulations demonstrate a deviation of place of excitation along the cochlear basilar membrane when an electrode array is present in the cochlear. In addition, a reduction of peak amplitude at the place of excitation on the BM may also be predicted by such simulation models. This implies that if an electrode array is present at the place of intended acoustic stimulation, the actual acoustic stimulation is moved towards a higher frequency and the amplitude of excitation may also be reduced. In an embodiment, simulations may also indicate that the frequency move and/or reduced amplitude may not be present if the acoustic stimulation site of excitation on the basilar membrane is at a location in the cochlear after the tip or after a certain distance away from the tip of the electrode array. In an embodiment, through simulations, it is possible to predict the amplitude shift and/or frequency shift that is applied to the first gain and/or first frequency, wherein the amplitude shift and/or frequency shift is equal or at least substantially equal and opposite to the reduction in gain and/or frequency move respectively. The amplitude shift and/or frequency shift is then stored in the conversion model as a conversion function. The speech processor, via signal processing, is configured to access the conversion function and apply the at least one of the amplitude shift and frequency shift to the first gain and/or first frequency to generate the second gain and/or second frequency in order to counteract a reduction in gain and/or frequency move, i.e. counteract the effect of change in mechanical properties of cochlea because of introduction of the electrode array. This would lead to a better representation of the acoustic stimuli when the patient uses the hearing aid system.

In one embodiment, the conversion function is based on two-stage standard audiometry test. The first stage includes performing a pre audiometry test prior to introduction of the implantable electrode array into the cochlea of the patient and the second stage includes performing a post audiometry test after the implantable electrode array into the cochlea of the patient. Respective threshold values (representing first gain) from the first stage and the second stage for a specific frequency are recorded and compared. The results of comparison reflecting at least one of the reduction in gain and/or frequency move as a result of introduction of the electrode array is then used to create a frequency specific conversion function comprising at least one of the amplitude shift and/or frequency shift, which is utilizable by the speech processor to counteract the deviation in frequency and/or gain that is produced by the implanted electrode array. Thus, the conversion function is based on change in at least one of the first gain and the first frequency of the acoustic stimulation in the patient in response to at least one of characteristics of the implantable electrode array. In another embodiment, the two stage standard audiometry test may be used on a sample population, the two stage standard audiometry test comprising a pre audiometry test and post audiometry test performed on the sample population and the obtained comparison results are averaged to determine the conversion function. Thus, the conversion function is based on an average of changes in at least one of the first gain and the first frequency of the acoustic stimulation in the sample population other than the patient in response to at least one of the characteristics of the implantable electrode array.

Thus, in an embodiment, the conversion function is based on variation in audiometric data for the patient prior to insertion of the cochlear array and after the insertion of the cochlear array within at least in the part of the residual frequency range. The variation may include at least one of a) a difference between the first gain at the first frequency prior to the insertion of the cochlear array and a second gain at the first frequency after the insertion of the cochlear array; and b) a difference between the first frequency corresponding to the first gain prior to insertion of the cochlear array and the second frequency corresponding to the first gain after the insertion of the cochlear array. The audiometric data for the patient may be obtained through conventionally known techniques such as pure tone audiometry. In view of the embodiment, a further embodiment includes a fitting method for customizing the second unit, which is selected from a group consisting of an acoustic hearing aid configured to provide an air conduction acoustic simulation and a bone conduction hearing aid configured to provide a bone conduction acoustic stimulation. The fitting method comprises aforementioned two-stage standard audiometry test. The fitting method, thus, allows for programming the second unit by taking into account the variation such that the second unit is programmed to provide the modified acoustic stimulation signal comprising at least one of a second gain at the first frequency, the first gain at a second frequency and the second gain at the second frequency, wherein the variation counteracts the effect of the implantable electrode array on mechanical properties of the cochlea.

In another embodiment, the conversion function is based on a computational model such as 3D-Finite element model of the inner ear, which is based on realistic anatomical properties of the cochlea (Bohnke F., Arnold W, 1999. 3*D finite element model of the human cochlea including fluid structure couplings. ORL J. Otorhinolaryngol relat. Spec.* 61 (5), 305-310). Other known computational models illustrating parametric 3D models of the cochlea may also be used. Post-operative (after cochlear implant surgery) changes on the mechanical properties of the cochlea and on the propagation of travelling wave based on frequency specific stimulation are investigated. In one embodiment, the results obtained in the model are compared to results obtained from the patient that still has residual hearing and is implanted with the implantable electrode array. The results of comparison reflecting at least one of the reduction in gain and frequency move as a result of introduction of the electrode array is then used to create a frequency specific conversion function comprising at least one of the amplitude shift and frequency shift, which is utilizable by the speech processor to counteract the deviation in frequency and/or gain that is produced by the implanted electrode array. Thus, in this embodiment, the conversion function is based on change in at least one of the first gain and the first frequency of the acoustic stimulation in the patient in response to at least one of characteristics of the implantable electrode array. In another embodiment, the results obtained in the model are compared to results obtained from a group of patients (sample population) that still has residual hearing at least in some overlapping residual frequency range of the patient with such group being implanted with the implantable electrode array. The result obtained from the sample population may be averaged to produce an average population result. The average results of comparison reflecting at least one of the reduction in gain and frequency move as a result of introduction of the electrode array is then used to create a frequency specific conversion function comprising at least one of the amplitude shift and frequency shift, which is utilizable by the speech processor to counteract the deviation in frequency and/or gain that is produced by the implanted electrode array. Thus, in this embodiment, the conversion function is based on an average change in at least one of the first gain and the first frequency of the acoustic stimulation in the sample population other than the patient in response to at least one of the characteristics of the implantable electrode array.

In an embodiment, it is useful to define at least approximate location of the electrode tip within the cochlea, i.e. until which location within the cochlea the electrode array extends because the effect on the mechanical properties of the cochlea is typically restricted to basilar membrane region that is adjacent to the electrode array. Nevertheless, in some situation, the effect may extend until a certain distance away from the tip of the electrode array. This may for example depend upon the characteristics of the electrode array. Therefore, the conversion model is configured to account for the location of the electrode tip within the cochlea. In one embodiment, the approximate electrode tip location is estimated during surgery from the insertion depth of the electrode. This determination of insertion depth during surgery may represent the insertion depth for the patient and/or an average insertion depth value for the sample population using implantable electrode array of same characteristics. Thus, in this embodiment, the conversion function is based on change in at least one of the first gain and the first frequency of the acoustic stimulation in the patient in response to at least one of characteristics of the implantable electrode array or in a sample population other than the patient in response to at least one of the characteristics of the implantable electrode array. Because, there is some variance on cochlea shapes across different patients, the measured insertion depth of the electrode (during surgery) may be a rough predictor of actual electrode tip location in the cochlea. Therefore, in another embodiment, the approximate electrode tip location is estimated using a scanning technique such as a CT scan of the patient or the sample population. This allows for more accurately predicting the location of the electrode tip in the cochlear by applying a parametric model of cochlea on the low resolution CT scan, the parametric model being derived from high resolution micro-CT scans of many cochleas. Thus, in this embodiment, the conversion function is based on change in at least one of the first gain and the first frequency of the acoustic stimulation in the patient in response to at least one of the characteristics of the implantable electrode array or in a sample population other than the patient in response to at least one of the characteristics of the implantable electrode array.

In an embodiment, the conversion function is based on change in at least one of the first gain and the first frequency of the acoustic stimulation in the patient in response to at least one of characteristics of the implantable electrode array. In another embodiment, the conversion function is based on an average change in at least one of the first gain and the first frequency of the acoustic stimulation in a sample population other than the patient in response to at least one of the characteristics of the implantable electrode array. In an embodiment, the phrase "sample population" may refer a group of people having a comparable profile of the patient. The comparable profile may include at least one of residual frequency range, age, gender, electrode array having at least one common characteristic. These characteristics may include one or a combination of a design of the implantable electrode array, mechanical properties of the implantable electrode array, insertion length of the implantable electrode array, distance of the implantable electrode array from the basilar membrane when the electrode array is located within the cochlea, and insertion technique for locating implantable electrode array into the cochlea.

In an embodiment, the characteristics of the implantable electrode array comprises one or a combination of a design of the implantable electrode array, mechanical properties of the implantable electrode array, insertion length of the implantable electrode array, distance of the implantable electrode array from the basilar membrane when the electrode array is located within the cochlea, and insertion technique for locating implantable electrode array into the cochlea. For example, the design of the electrode array may include whether the electrode array has modiolus-hugging capability, or whether the electrode array is straight.

In position within the cochlea, the distance between modiolus hugging electrode array and the basilar membrane is smaller than that between the basilar membrane and the straight electrode, which are usually located at the outer circumference of the scala tympani. The mechanical properties may include thickness of the electrode array, material of the electrode array, length of the electrode array, uniform or varying lengthwise stiffness of the electrode array. Therefore, for a patient, the modification values (amplitude shift and/or frequency shift) required to generate the modified acoustic stimulation for the implantable modiolus hugging stiffer material electrode array will be higher than a straight design thinner (flexible) electrode array. The skilled person would appreciate that the gain and/or frequency shift values is proportion to increase in stiffness of the basilar membrane and is caused typically in basilar membrane region that is proximal including adjacent to the electrode array, which causes mechanical pressure of the electrode array against the basilar membrane. The thickness of the electrode array may include a uniform thickness electrode array or a varying thickness electrode array comprising a thickness reducing from basal end of the electrode to the tip of the electrode array, the basal end of the end being proximal to base of the cochlea in implanted position. The stiffness of the varying thickness electrode array typically reduces along the length of the electrode array from the basal end to the tip.

In an embodiment, the amplitude shift and/or frequency shift is a function of distance of the electrode array from the basilar membrane when the electrode array is in implanted position. The distance may relate to the distance from a region of the basilar membrane that corresponds to the first frequency. In another embodiment, the amplitude shift and/or frequency shift is a function of first frequency. For example, a higher first frequency value may illustrate a higher frequency shift compared to a lower first frequency value. In another example, the amplitude shift and/or frequency shift is a function of flexibility of the electrode array.

In an embodiment, the conversion function is configured to be updated in accordance with variations in characteristics of the implantable electrode array over time. The updated conversion function comprises at least one of an updated amplitude shift and updated frequency shift. The updated gain shift and/or updated frequency shift may be stored in the memory and replaces the amplitude shift and frequency shift. The speech processor is configured to access the updated conversion function to counter time-based variation in the mechanical properties of cochlea. The speech processor is configured to modify the acoustic stimulation in accordance with the at least one of the updated amplitude shift and updated frequency shift in order to generate an updated modified acoustic stimulation signal that is delivered to the cochlea using the second unit for producing sound perception in the residual frequency range. The updated conversion function may be determined in accordance with the technique disclosed earlier such as using two-staged audiometry test on the patient and/or using the computational model based test on the patient and/or insertion depth estimation using scanning technique on the sample population. Additionally or alternatively, the updated conversion function may be determined in accordance with the technique disclosed earlier such as using two-staged audiometry test on the sample population and/or computation model based test on the sample population and/or insertion depth estimation using scanning technique on the sample population. In this embodiment, as the updated conversion function is based on the sample population other than the patient, the patient may not be expected to visit the hearing care professional (HCP) location for the conversion model to be updated. The hearing aid system is adapted to receive the updated conversion function remotely from the HCP location. In one sub-embodiment, a remote device such as smartphone or laptop is adapted to receive the updated conversion function from the HCP location using a Ion range network between the HCP location and the remote device, which is communicatively coupled to the speech processor over a short range network such as Bluetooth. The remote device is adapted to store the received updated conversion model in a memory of the remote device. The speech processor may access the updated conversion table stored in the memory of the remote device for generating the updated modified acoustic stimulation signal. In another sub embodiment, a remote device such as smartphone or laptop is adapted to receive the updated conversion function from the HCP location using a long range network between the HCP location and the remote device, which is communicatively coupled to the speech processor. The hearing aid system is adapted to receive, over a short range network such as Bluetooth, the updated conversion model, which is stored in the memory of the hearing aid system. The speech processor may access the updated conversion table that is stored in the memory for generating the updated modified acoustic stimulation signal.

In various embodiments as described in the preceding sections, the speech processor is defined as being configured to modify the acoustic stimulation signal into the modified acoustic signal in accordance with effect of an implantable electrode array on mechanical properties of cochlea of the patient. In one embodiment, the acoustic stimulation signal includes a modulated electrical signal that is produced in dependence on the audiogram of the patient, that is, by applying a modulation to the microphone signal to compensate for a hearing impairment of the patient. The modulation comprises applying the first gain at the first frequency comprised in the residual frequency range to the microphone signal. In this embodiment, the modified acoustic stimulation signal is produced by further modulating the acoustic stimulation signal in accordance with the conversion function that is accessible by the speech processor. In another embodiment, the acoustic stimulation signal includes parameters such as frequency specific amplification value (i.e. the first gain at the first frequency) independent of generation of the modulated electrical signal as required in the preceding embodiment. In this embodiment, the modified acoustic stimulation signal is produced by accessing the conversion function and utilizing the second gain (or amplitude shift) and/or second frequency (or frequency shift) corresponding to the first gain and first frequency to modulate the microphone signal and directly generating the modified acoustic stimulation signal without generating the modulated electrical signal. The phrase "generate a modified acoustic stimulation signal by modifying the acoustic stimulation signal" or similarly worded phrases in the text is intended to cover at least one or both embodiments recited in this paragraph.

According to an embodiment, a method for producing a dual-mode stimulation at a cochlea of the patient is disclosed. The method includes processing, at a speech processor communicatively coupled to a microphone, a microphone signal received at the speech processor for producing an electrical stimulation signal and an acoustic stimulation signal. The method further includes generating, at the speech processor, a modified acoustic stimulation signal by modifying the acoustic stimulation signal at least for a part of a residual frequency range of a patient in dependence on effect of an implantable electrode array on mechanical properties of cochlea of the patient. Thereafter, the electrical stimulation based on the electrical stimulation signal to a cochlea within a non-residual frequency range of the patient and the modified acoustic stimulation based on the modified acoustic stimulation within the residual frequency range is provided to the cochlea of the patient using a first unit and a second unit respectively. The first unit includes a cochlear implant communicatively coupled to the speech processor, wherein the cochlear implant comprising the implantable electrode array configured to be located within a cochlea of the patient. The second unit is communicatively connected to the speech processor. The second unit may be selected from a group consisting of an acoustic hearing aid configured to provide air conduction acoustic stimulation and a bone conduction hearing aid configured to provide a bone conduction acoustic stimulation.

In an embodiment, the method further includes generating, using the speech processor, the acoustic stimulation signal comprising a first gain corresponding to a first frequency comprised within the residual frequency range in accordance with an audiogram of the patient. Thereafter, the speech processor modifies at least one of the first gain and the first frequency to generate the modified acoustic stimulation signal comprising at least one of a second gain at the first frequency, the first gain at a second frequency and the second gain at the second frequency.

In an embodiment, the modification of the acoustic stimulation signal is based on a conversion model comprising a conversion function that includes at least one of an amplitude shift from the first gain to the second gain and a frequency shift from the first frequency to the second frequency for at least substantially countering the effect of the implantable electrode array on mechanical properties of the cochlea of the patient.

In another embodiment, a method for customizing a hearing aid system configured to produce an acoustic stimulation and an electrical stimulation to a cochlea of a patient is disclosed. The method includes determining a residual frequency range for a patient, determining whether mechanical properties of a cochlea including basilar membrane of the patient is effected due to the presence of an implantable electrode array into the cochlea. The method further includes predicting the effect of the implantable electrode array on mechanical properties of cochlea of the patient; and creating a conversion model comprising a conversion function that is stored in a memory that is accessible by a speech processor. The conversion function comprises at least one of an amplitude shift from the a first gain to a second gain and a frequency shift from a first frequency to a second frequency for at least substantially countering the effect of the implantable electrode array on mechanical properties of the cochlea of the patient, the first gain and first frequency being based on an audiogram of the patient. Furthermore, the speech processor configured to process a received microphone signal for producing an electrical stimulation signal and an acoustic stimulation signal, the speech processor being further configured to generate a modified acoustic stimulation signal by modifying the acoustic stimulation signal at least for a part of a residual frequency range of the patient in dependence on effect of an implantable electrode array on mechanical properties of cochlea of the patient.

In one embodiment, the conversion model is stored in a memory comprised in the speech processor casing. Additionally or alternatively, the conversion model is stored in a remote memory separate from the speech processor unit through a wireless link such as Bluetooth for example accessing memory of a communicatively coupled smartphone.

The preceding embodiment may be implemented using one or more of the features disclosed in the preceding sections. For example, the means for determining the residual frequency range may be performed using standard audiometric measurement procedures. Similarly, determining the effect of an implantable electrode array on mechanical properties of cochlea and creation of conversion model comprising the conversion function may be implemented using two stage audiometry test and/or computational model on the patient or sample population. The modification of the acoustic stimulation signal to the modified acoustic stimulation signal may be based on at least one of the frequency shift and amplitude shift of the conversion function.

In an embodiment, a computer readable medium for storing a computer readable instructions which when executed causes the speech processor that is communicatively coupled to a microphone to process a microphone signal received at the speech processor for producing an electrical stimulation signal and an acoustic stimulation signal; generate a modified acoustic stimulation signal by modifying the acoustic stimulation signal at least for a part of a residual frequency range of a patient in dependence on effect of an implantable electrode array on mechanical properties of cochlea of the patient; provide the electrical stimulation based on the electrical stimulation signal to a cochlea within a non-residual frequency range of the patient using a first unit comprising a cochlear implant communicatively coupled to the speech processor, the cochlear implant comprising the implantable electrode array configured to be located within a cochlea of the patient; and provide the modified acoustic stimulation based on the modified acoustic stimulation signal to the cochlea within the at least in the part of the residual frequency range using a second unit communicatively coupled to the speech processor.

In an embodiment, the computer readable medium for storing a computer readable instructions which when executed causes the speech processor to generate the acoustic stimulation signal comprising a first gain corresponding to a first frequency comprised within the residual frequency range in accordance with an audiogram of the patient; and modify at least one of the first gain and the first frequency to generate the modified acoustic stimulation signal comprising at least one of a second gain at the first frequency, the first gain at a second frequency and the second gain at the second frequency, wherein the modification counteracts the effect of the implantable electrode array on mechanical properties of the cochlea.

In an embodiment, the computer readable medium for storing a computer readable instructions which when executed creates the conversion table, which has characteristics explained in different embodiments of the disclosure. Execution of the computer readable instructions allows for storing the conversion table in a memory of the second unit.

In an embodiment, the computer readable medium for storing a computer readable instructions which when executed causes the speech processor to access a conversion model stored in a memory to generate the modified acoustic stimulation signal, the modified acoustic stimulation signal being configured to at least substantially counter the effect of the implantable electrode array on mechanical properties of the cochlea of the patient.

According to an embodiment, the computer readable medium stores a computer readable instructions which when executed causes the speech processor to perform additional tasks that are described in various embodiments the disclosure.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 2A illustrates an acoustic stimulation produced by an acoustic hearing aid;

FIG. 2B illustrates an electrical stimulation produced by a cochlear implant;

FIG. 3A illustrates variation in acoustic stimulation for a dual stimulation mode hearing aid system comprising an acoustic hearing aid and cochlear implant;

FIG. 3B illustrates acoustic stimulation for a dual stimulation mode hearing aid system comprising an acoustic hearing aid and cochlear implant according an embodiment of disclosure;

DETAILED DESCRIPTION

The detailed description set forth below in connection with the appended drawings is intended as a description of non-limiting example embodiments of the method and system according to the present disclosure. In accordance to an embodiment, there is provided a dual stimulation hearing aid system comprising the features of claim 1 below. Advantageous features are set out in the sub-claims.

Following disclosure is defined in terms of a dual stimulation mode hearing aid system where the first unit comprises a cochlear implant adapted to produce electrical stimulation and the second unit comprises an acoustic hearing aid for producing an air conduction acoustic stimulation. However, the disclosure is also applicable for a dual stimulation mode hearing aid system where the first unit comprises a cochlear implant adapted to produce electrical stimulation and the second unit comprises a bone conduction hearing aid configured to provide a bone conduction acoustic stimulation.

In one embodiment, the disclosure represents a scenario where the first unit and the second unit a physically positioned proximal to the same ear. In another embodiment, the disclosure represents a scenario where the first unit and the second unit are physically positioned on opposite ear, i.e. bilaterally positioned. However, in both the preceding embodiments, the first unit and the second unit are configured to stimulate the same cochlea.

Figure 1:
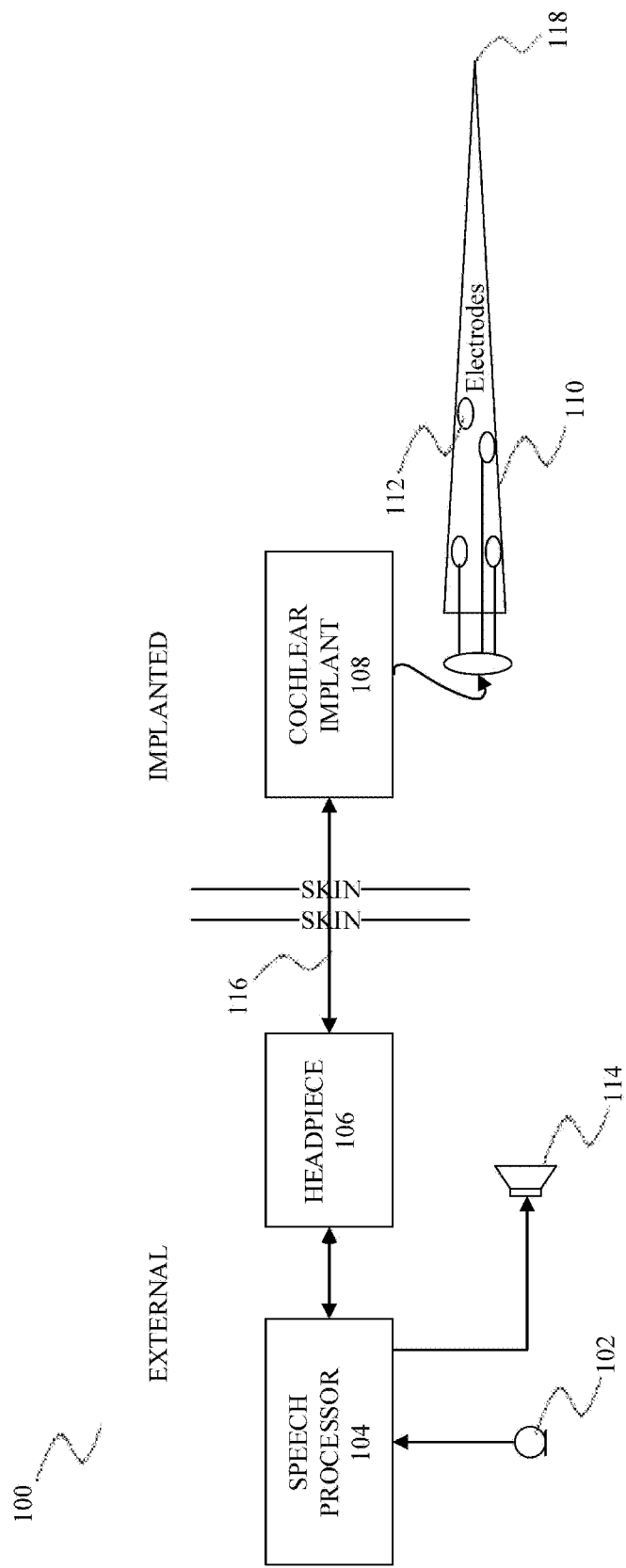
FIG. 1 illustrates a dual stimulation mode hearing aid system comprising an acoustic hearing aid and cochlear implant.

FIG. 1 illustrates an exemplary dual stimulation mode hearing aid system such as an EAS system 100. The hearing aid system 100 may include a microphone 102, an EAS speech processor 104, a headpiece 106 having a transmitter coil disposed therein, a cochlear implant 108, an implantable electrode array 110 with a plurality of electrodes 112 disposed thereon, and a speaker 114 (also referred to as a "receiver"). Additional or alternative components may be included within system 100 as may serve a particular implementation.

As shown, various components of system 100 may be located external to the patient including, but not limited to, microphone 102, EAS speech processor 104, headpiece 106, and receiver 114. Various components of the system 100 may be implanted within the patient including, but not limited to, cochlear implant 108 and electrode array 110. As will be described in more detail below, additional or alternative components may be included within system 100 as may serve a particular implementation. The components shown in FIG. 1 will now be described in more detail.

Microphone 102 may be configured to detect audio signals (i.e., sound) presented to the patient. Microphone 102 may be implemented in any suitable manner. For example, microphone 102 may include a "T-Mic" or the like that is configured to be placed within the concha of the ear near the entrance to the ear canal and/or in a unit held at the pinna behind-the-ear of the patient. The microphone is selectively attached to EAS speech processor 104. Additionally or alternatively, microphone 102 may be implemented by one or more microphones disposed within headpiece 106, one or more microphones disposed within EAS speech processor 104, and/or any other suitable microphone as may serve a particular implementation.

EAS speech processor 104 (i.e., one or more components included within EAS speech processor 104) may be configured to direct cochlear implant 108 to generate and apply electrical stimulation (also referred to herein as "stimulation current" or "electrical energy") representative of one or more electrical stimulation signal corresponding to one or more band limited microphone signal within the non-residual frequency range to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, EAS speech processor 104 may process the one or more band limited microphone signals within the non-residual frequency range in accordance with a selected sound processing strategy or program to generate appropriate stimulation parameters for controlling cochlear implant 108. EAS speech processor 104 may include or be implemented by a behind-the-ear ("BTE") unit, a body worn device, and/or any other sound processing unit as may serve a particular implementation.

In some examples, EAS speech processor 104 may wirelessly transmit stimulation parameters (e.g., in the form of data words included in a forward telemetry sequence) and/or power signals to cochlear implant 108 by way of a wireless communication link 116 between headpiece 106 and cochlear implant 108. It will be understood that communication link 116 may include a bi-directional communication link and/or one or more dedicated unidirectional communication links.

EAS speech processor 104 may be further configured to direct speaker 114 to apply acoustic stimulation representative of microphone signal within the residual frequency range. Thus, the speaker 114 may present an amplified version of microphone signal within the residual frequency range to the patient. The speaker 114 may be communicatively coupled to the speech processor 104 in any suitable manner. For example, the speaker 114 may be at least partially disposed within the housing of headpiece module 106 of speech processor casing and the amplified sound is delivered from the speaker 114 to the eardrum via a sound tube. Alternatively, speaker 114 may be at least partially integrated into an earmold configured to be located within the outer ear of the patient and communicatively coupled to speech processor 104 with one or more wires.

The system 100 may be used when the patient has some residual hearing in the residual frequency range (e.g., below 1000 Hz) and severe hearing loss in the non-residual frequency range (e.g., above 1000 Hz). To this end, EAS sound processor 104 may direct cochlear implant 108 to apply electrical stimulation representative of sound included in a the non-residual frequency range to one or more stimulation sites within the patient (e.g., within the cochlea of the patient) by way of one or more electrodes 112 included in electrode array 110 and speaker 114 to apply acoustic stimulation representative of audio content included in the residual frequency range to the patient. In some alternative embodiments, the patient may have non-contiguous frequency regions of residual hearing. For example, the patient may have non-contiguous regions of damaged outer hair cells, which may result in the patient having residual hearing in non-adjacent frequency bands, system 100 may also be used for these types of patients.

Headpiece 106 may be communicatively coupled to speech processor 104 and may include an external antenna (e.g., a coil and/or one or more wireless communication components) configured to facilitate selective wireless coupling of the speech processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between the speech processor 104 and cochlear implant 108 via a communication link 116 (which may include a bi-directional communication link and/or one or more dedicated uni-directional communication links as may serve a particular implementation).

Cochlear implant 108 may include any type of implantable stimulator that includes a communicatively coupled implantable electrode 110 array that may be positioned within cochlea of the patient.

In some examples, cochlear implant 108 may be configured to generate electrical stimulation representative of an microphone signal processed by the speech processor 104 (e.g., an audio signal detected by microphone 102) in accordance with one or more stimulation parameters transmitted thereto by EAS speech processor 104. To this end, cochlear implant 108 may include one or more current generators.

FIG. 2A illustrates an acoustic stimulation produced by an acoustic hearing aid. In an embodiment, the acoustic hearing aid comprises a speech processor unit 206 comprising a speech processor (not shown) and a microphone (not shown) that is adapted is receive sound 204 from a sound source 202. The speech processor unit 206 may be positioned behind the ear 206 using an ear hook. The receiver 114 may be positioned in the canal 208 and electrically coupled to the speech processor using a wire 212. The sound 204 at the microphone is transformed into a microphone signal, which is processed by the speech processor. The speech processor applies frequency specific amplification to the sound and delivers the amplified signal to the receiver 114. The receiver sends the amplified signal as acoustic stimulation signal through middle ear 216 to cochlea 218 of the inner ear. The inner ear comprises basilar membrane 220 that becomes progressively wider and more flexible from base of the cochlea to the apex. As a result, each area of the basilar membrane vibrates preferentially to a particular sound frequency. High-frequency sound waves cause maximum vibration of the area of the basilar membrane nearest to the base of the cochlea; medium-frequency waves affect the centre of the membrane; and low-frequency waves preferentially stimulate the apex of the basilar membrane. In response to the acoustic stimulation, the cochlear fluid oscillates in phase with the stimulus, causing the whole basilar membrane to vibrate at the stimulating frequency. However, because the membrane varies along its length, there is one place along the membrane where the resonant frequency of the membrane matches the stimulus frequency and this place 222 shows the maximum amount of vibration. Thus, each frequency can be mapped to a single place of maximum vibration. This is called a tonotopic or frequency to place mapping. Within the organ of corti are specialised vibration-sensitive cells called hair cells. These have projecting cilia that shear against the tectorial membrane when the basilar membrane vibrates. Bending of the cilia releases neurotransmitter which passes into the synapses of one or more nerve cells which fire to indicate vibration. The amount of firing is thus related to the amount of vibration, so that the overall pattern of nerve excitation from the organ of *Corti* also follows the place principle. Since neurotransmitter is only released when the cilia are bent in one direction, firing tends to be in phase with basilar membrane movement.

FIG. 2B illustrates an electrical stimulation produced by a cochlear implant system. The cochlear implant system comprises an external part and an internal part. The external part comprises a speech processor unit 206 comprising speech processor and a microphone, which is adapted to receive sound from 204 from a sound source 202 and generate a microphone signal. The speech processor unit 206 may be positioned at an ear 206 using an ear hook as a behind the ear type casing. The speech processor processes the received microphone signal and using a headpiece 106 comprising a transmitter coil sends the processed microphone signal to a cochlear implant stimulator unit 108 that includes a receiver coil adapted to receive the transmitted processed signal. The stimulator 108 is adapted to utilize the received processed signal and generate an electric pulse in accordance with a mapping function, which defines an electric stimulation level (% charge) of an electric current pulse for an electrode as a function of the stimulation level of the processed signal. The generated electric pulse is provided to the implanted electrode 112 of the implantable electrode array 110, which sends impulses 224 by way of the auditory nerve to the brain, which recognizes the signals as sound. The electrode stimulation signal is frequency band specific and are associated with a particular electrode of an electrode array. Each electrode of the plurality of electrodes include a different frequency distribution as defined by a corresponding audio frequency range. For example, the electrode array may include 20 implanted electrodes where electrode 1 close to the base of the cochlea associated with a frequency range between 6800 Hz to 8000 Hz, electrode 2 associated with a frequency range between 5800 Hz to 6800 Hz and so on with electrode being closest to the apical region and covering frequency range between say 200 Hz to 300 Hz. It is apparent that the electrode array may include less or more than 20 electrodes and the frequency distribution for the electrodes may vary. The electrodes corresponding to the associated frequency range are frequency-place matched along length of the cochlea such that an electric pulse carrying information of a specific frequency band activates the corresponding electrode, and in effect a specific frequency region of the auditory nerve along the cochlea. 118 represents tip of the implanted electrode array and 220 the basilar membrane of the cochlea.

FIG. 3A illustrates variation in acoustic stimulation for a dual stimulation mode hearing aid system comprising an acoustic hearing aid and cochlear implant. The sound 204 from a sound source 202 is detected by a microphone, which may be either comprised in the speech processor unit 302 or positioned at a different location like pinna or in the ear canal. The microphone transforms the detected sound to a microphone signal. The speech processor unit 302, positionable at ear 206, comprises a speech processor that processes the microphone signal and generates an electrical stimulation signal and an acoustic stimulation signal. The electrical stimulation signal is transmitted to the cochlear implant 108 via the headpiece 106 and delivered as electric pulses to the auditory nerve using electrodes 112 of the implanted electrode 110. The acoustic stimulation signal is transmitted from the speech processor to the receiver 114 using a wire 212. The acoustic stimulation is delivered to the auditory via the air pathway of outer ear, middle ear and inner ear. For a hearing aid system that is configured to provide both electrical stimulation and acoustic stimulation, an introduction of the implantable electrode in the cochlea of the patient may alter mechanical properties of the inner ear such as stiffness of basilar membrane. Generally, the stiffer the basilar membrane, the higher the resonant frequency. Therefore, introduction of the electrode array affects the natural tonotopic mapping of the basilar membrane. This result in variation in stimulation in at least one of resonant frequency 112 of a region 222 of basilar membrane 220 and also possible in vibration levels 114 of basilar membrane in comparison to when same stimulation level is applied to same cochlea when the electrode array is absent. This variation in resonant frequency location and/or vibrations of basilar membrane affects basic pitch determining mechanism, thus negatively affecting perception of sound. Therefore, restoration of pitch discrimination when electrode array is present in the cochlea becomes useful. 232 represents insertion depth of the electrode array within the cochlear and also corresponds to length (first length) of basilar membrane adjacent to the electrode array. 234 represents a second length of the basilar membrane. In one embodiment, the increase in stiffness is along a length of basilar membrane that is adjacent to the electrode array. This may be because of the close contact of the electrode array with the basilar membrane at least in some distinct section of the basilar membrane such as at middle turns of the cochlea. In another embodiment, the increase in stiffness of basilar membrane is along a first length of basilar membrane that is adjacent to the electrode array and a second length of the basilar membrane that extends a distance beyond the first length. The second length is continuous to the first length and extends beyond a tip of the electrode array until a certain distance away from the tip. In these embodiments, the increase in stiffness along the first length and/or second length is dependent upon characteristics of the implantable electrode array.

FIG. 3B illustrates acoustic stimulation for a dual stimulation mode hearing aid system comprising an acoustic hearing aid and cochlear implant according an embodiment of disclosure. The sound 204 from a sound source 202 is detected by a microphone, which may be either comprised in the speech processor unit 302 or positioned at a different location like pinna or in the ear canal. The microphone transforms the detected sound to a microphone signal. The speech processor unit 302, positionable at ear 206, comprises a speech processor that processes the microphone signal and generates an electrical stimulation signal and an acoustic stimulation signal. The electrical stimulation signal is transmitted to the cochlear implant 108 via the headpiece 106 and delivered as electric pulses 224 to the auditory nerve using electrodes 112 of the implanted electrode 110. As indicated earlier introduction of the electrode array 110 into the cochlea affects mechanical properties of the cochlear leading to an altered sound perception compared to if the cochlear implant was absent. To overcome this, the speech processor is further configured to modify the acoustic stimulation signal to generate a modified acoustic stimulation signal that is transmitted from the speech processor to the receiver 114 using a wire 212. The modified acoustic stimulation is delivered to the auditory via the air pathway of outer ear, middle ear and inner ear. The modified acoustic stimulation signal may be such that the variation due to the effect of the implanted electrode array on the mechanical properties of the cochlea is compensated. For example, 222 represents a location on basilar membrane corresponding to a resonant frequency f1 (first frequency), which is a frequency of an acoustic stimulation signal. However, because of the presence of the electrode array, the location 222 would correspond to a resonant frequency lower than f1. Therefore, stimulation signal having a frequency f1 would not stimulate location 222 on the basilar membrane but will rather stimulate a location 228 (towards basal location relative to 222) because of change in mechanical properties such as stiffness of location 228, which now represents the resonant frequency f1. The change in mechanical properties of cochlea affects the place-frequency mapping in cochlea and produces sub-optimal perception because of deterioration in pitch discrimination. Therefore, an embodiment of the disclosure proposes utilizing the modified acoustic stimulation signal having a second frequency f2, which is lower than the first frequency f1 by a frequency shift value that is equal to a frequency shift Δf=(f2'−f1). Stimulating the basilar membrane at location 226 that corresponds to a frequency that is lower than the desired stimulation frequency and by a value of Δf allows for compensating for the variation in place-frequency mapping introduced because of the presence of the implanted electrode array. In another example that is combinable with the earlier example, the skilled person would appreciate that comparable principle may be used when applying gain to the microphone signal. In other words, introduction of the electrode array may reduce the vibration producing capability of the basilar membrane. Therefore, if acoustic stimulation signal required a gain (first gain) of L1 at frequency f1 in absence of the electrode array to compensate for patient loss, and introduction of the electrode array reduces the vibration corresponding to gain L2', then the gain L2 (second gain) of the modified acoustic stimulation is larger than the first gain L1 and by a value defining amplitude shift ΔL=L1−L2'. Stimulating the basilar membrane with a gain that is higher than the desired gain level L1 and by a value of ΔL allows for compensating for the variation in vibration of basilar membrane introduced because of the presence of the implanted electrode array.

Figure 7:
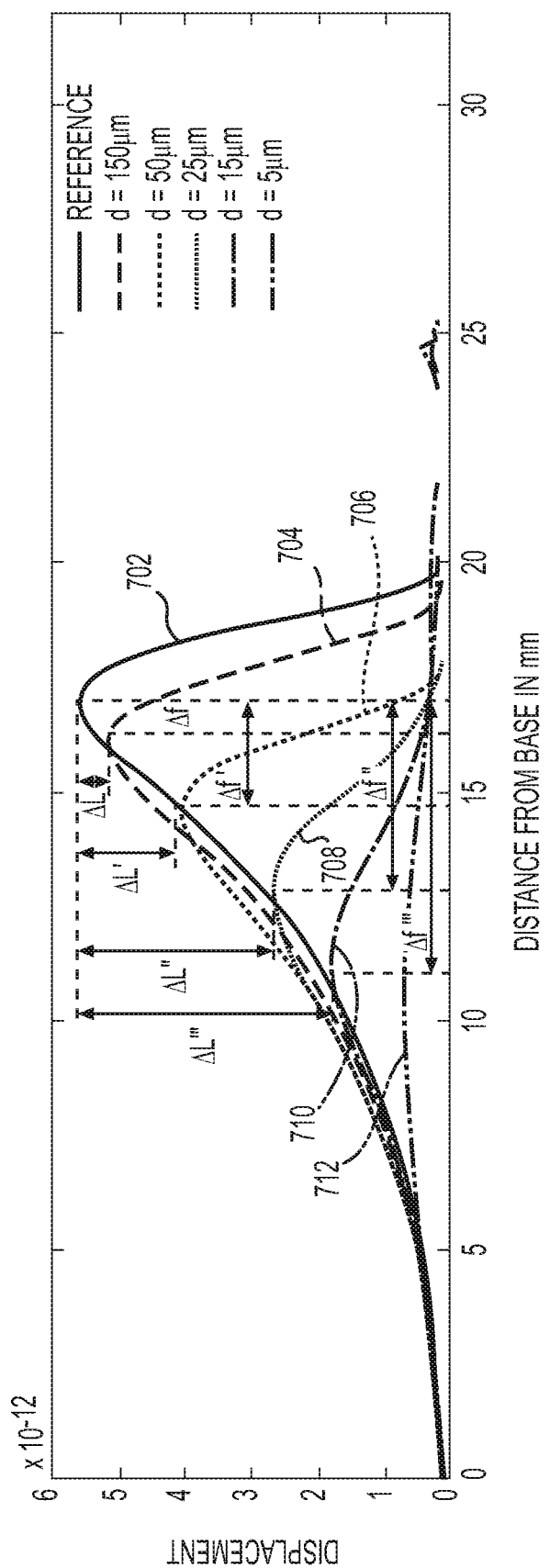
FIG. 7 illustrates effect of the implanted electrode array on mechanical properties of the basilar membrane according to an embodiment.
Figure 8:
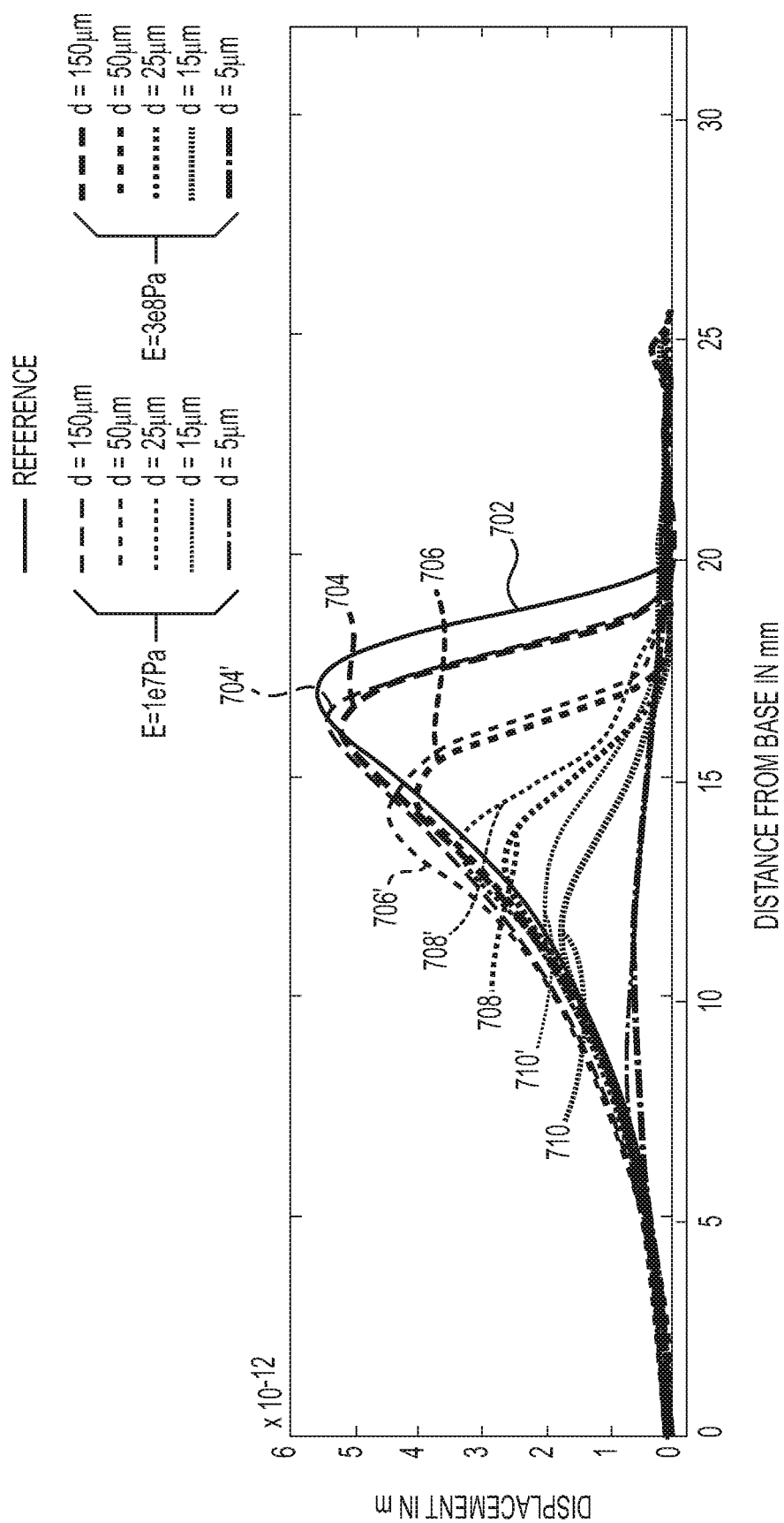
FIG. 8 illustrates effect of the implanted electrode array on mechanical properties of the basilar membrane according to an embodiment.

The effect of implanted electrode on mechanical properties of cochlea is further illustrated by way of an example in FIG. 7 to FIG. 8. The chart represents distance from base of cochlea on the x-axis, which in view of tonotopic structure of cochlea also represents characteristic frequency along the cochlea starting from high frequency at base towards low frequency at apex. The y-axis represents displacement of the basilar membrane and in particular peak amplitude of an envelope of the travelling wave at a resonance frequency.

FIG. 7 illustrates effect of the implanted electrode array on mechanical properties of the basilar membrane according to an embodiment. 702 represents an envelope of travelling wave in response to an acoustic stimulation signal having a first gain at stimulation frequency of 1 kHz tone in absence of the implanted electrode array. 704, 706, 708, 710, 712 represents envelopes of travelling wave in response to an acoustic stimulation signal having the first gain at stimulation frequency of 1 kHz tone when the electrode array is present in the cochlea and distance (d, also illustrated in FIG. 3B) between the electrode array and basilar membrane is systematically reduced. In the illustrated embodiment, it is apparent that introduction of the electrode array reduces gain (ΔL, ΔL', ΔL'', ΔL''', not shown for 712) and introduces a basal shift (Δf, Δf', Δf'', Δf''', not shown for 712) in frequency, i.e. deviation of frequency towards higher frequency region of cochlea for the travelling wave (704, 706, 708, 710) in response to an acoustic stimulation signal of stimulation frequency of 1 kHz tone. It is also apparent, that for same electrode array, greater the distance (d) between an electrode array and basilar membrane, smaller the effect of the electrode array on the values of Δs—see the table below:

TABLE 1

Effect of electrode array as a function of distance (d)

| Travelling wave | Distance (d) | Gain reduction | Basal shift |
| --- | --- | --- | --- |
| 704 | 150 μm | ΔL | Δf |
| 706 | 50 μm | ΔL' | Δf' |
| 708 | 25 μm | ΔL'' | Δf'' |
| 710 | 15 μm | ΔL''' | Δf''' |

The skilled person would appreciate that characteristics other than distance (d) of the electrode array may be utilized for generating desired stimulation frequency specific gain reduction and/or basal shift values, which may be then utilized as amplitude shift and/or frequency shift to generate the modified acoustic stimulation signal. For example, with an implanted electrode array placed at a distance of 50 μm from basilar membrane region that naturally relates to 1 kHz, the modified acoustic stimulation would require a second gain (=first gain+amplitude shift ΔL') and second frequency (=first frequency (1 kHz)−frequency shift Δf) for producing same perception stimulation corresponding to travelling wave 702, that represents the acoustic stimulation at first gain at first frequency (1 kHz) in absence of the implanted electrode array.

In an embodiment, only one of the two effects such as reduction in gain may be observed. This may be case when reduction of peak amplitude may be present when the travelling wave peak region is apical to the tip of the electrode.

In another embodiment, the amplitude shift and/or frequency shift is a function of flexibility of the electrode array. This is shown in FIG. 8, which illustrates effect of the implanted electrode array on mechanical properties of the basilar membrane. The effect of electrode flexibility on the travelling wave is investigated by reducing Young's modulus (E) of the electrode array by a factor of 30, thus increasing the flexibility. Electrode to basilar membrane distance is changed similarly to the chart of FIG. 8 from which the results are indicated here by dashed lines for comparison. It is apparent that amplitude shift and/or frequency shift is a function of flexibility as one of the electrode array. For example, with same distance (d), the amplitude shift is lower for a more flexible electrode array (see pake amplitude of 704' vis-a-vis 704 or 706' vis-a-vis 706 or 708' vis-a-vis 708 or 710' vis-a-vis 710. The frequency shift may remain unchanged, for example 704' vis-a-vis 704 or is higher 706' vis-a-vis 706 or is lower 710' vis-a-vis 710.

In one embodiment, the residual frequency range and the non-residual frequency range are continuous. For example, FIG. 3B illustrates the non-residual frequency range 228 and the residual frequency range 230. It would be apparent to the skilled person that the non-residual frequency range may be discontinuous. Similarly, the residual frequency range may be non-contiguous. In other words, the residual frequency range and non-residual frequency range may be interleaved with each other. In one embodiment, at least a part of the residual frequency range is adjacent to length of the implanted electrode array 110, as shown in FIG. 3B. Having the electrode array adjacent to the residual frequency range may be useful in scenarios where at least a part of the residual hearing is lost in future in the part of basilar membrane that is adjacent to the electrode array. This may happen as a consequence of the cochlear implant surgery or over time due to aging. This allows for electrical stimulation of the residual frequency range, adjacent to the electrode array, that in future become part of the non-residual frequency range and may be stimulated electrically using the cochlear array rather than by acoustic stimulation.

In another embodiment, the residual frequency range is non-overlapping with the length of the electrode array.

Figure 4:
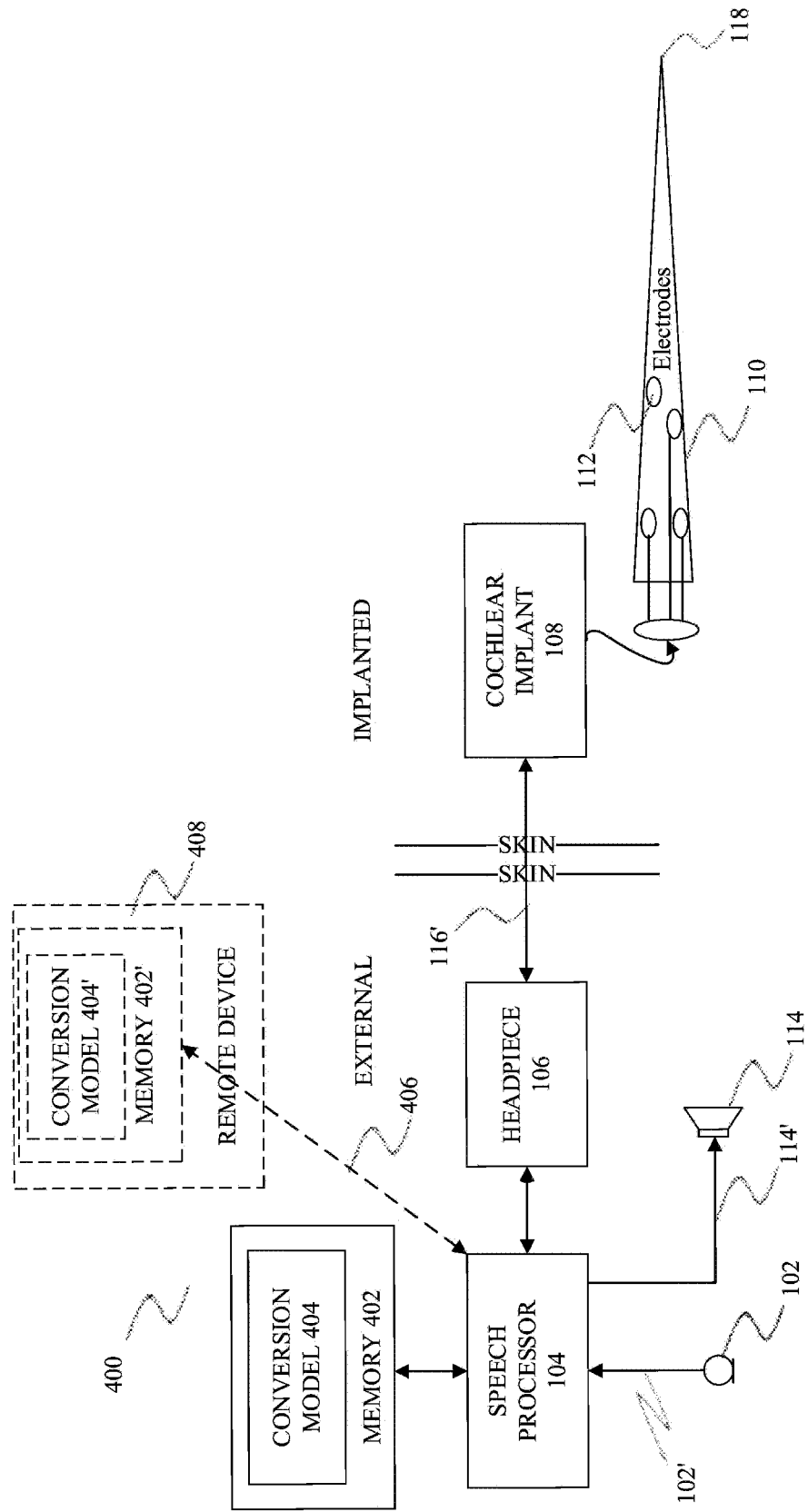
FIG. 4 illustrates a dual stimulation mode hearing aid system comprising an acoustic hearing aid and cochlear implant according to an embodiment of the disclosure.

FIG. 4 illustrates a dual stimulation mode hearing aid system comprising an acoustic hearing aid and cochlear implant according to an embodiment of the disclosure. The hearing aid system 400 includes all the features of earlier described heading aid system 100 (see FIG. 1). However, the speech processor 104 of the hearing aid system 400 is at least further configured to generate a modified acoustic stimulation. For this purpose, additional components may be provided such as a memory 402/402' comprising a conversion model 404/404'. The hearing aid system 400 includes a speech processor 104 communicatively coupled to a microphone 102 and configured to process a microphone signal 102' received at the speech processor 104 for producing an electrical stimulation signal 116' and an acoustic stimulation signal, the speech processor being further configured to generate a modified acoustic stimulation signal 114' by modifying the acoustic stimulation signal at least for a part of a residual frequency range (FIG. 3B, 230) of a patient in dependence on effect of an implantable electrode array 110 on mechanical properties of cochlea of the patient. The system further includes a first unit comprising a cochlear implant 108 communicatively coupled to the speech processor 104, the cochlear implant comprising the implantable electrode array 110 configured to be located within a cochlea of the patient and to provide the electrical stimulation based on the electrical stimulation signal to a cochlea within a non-residual frequency range (FIG. 3B, 228) of the patient; and a second unit 114 communicatively coupled to the speech processor 104 and adapted to provide the modified acoustic stimulation based on the modified acoustic stimulation signal 114' to the cochlea within the at least in the part of the residual frequency range (FIG. 3, 230).

In one embodiment, the second unit 114 is selected from a group consisting of an acoustic hearing aid configured to provide an air conduction acoustic simulation and a bone conduction hearing aid configured to provide a bone conduction acoustic stimulation.

In an embodiment, the effect of the electrode array 110 on the mechanical properties of cochlea (FIG. 2B, 218) comprises change in integrity of fine structures in the cochlea due to presence of the electrode array 110 in the cochlea, thereby affecting the mechano-electric transduction characteristics of the cochlea at least in the part of the residual frequency range (FIG. 3B, 230).

In an embodiment, the effect of the electrode array 110 on the mechanical properties of cochlea (FIG. 2B, 218) comprises an increase in stiffness of at least a part of basilar membrane (FIG. 2B, 220) of the cochlea due to presence of the electrode array 110 in the cochlea.

In an embodiment, the speech processor 104 is configured to generate the acoustic stimulation signal comprising a first gain L1 corresponding to a first frequency (FIG. 3B, f1) comprised within the residual frequency range (FIG. 3B, 230) in accordance with an audiogram of the patient. Additionally, the speech processor is also configured to modify at least one of the first gain L1 and the first frequency (FIG. 3B, f1) to generate the modified acoustic stimulation signal comprising at least one of a second gain L2 at the first frequency (FIG. 3B, f1), the first gain L1 at a second frequency (FIG. 3B, f2) and the second gain L2 at the second frequency (FIG. 3B, f2), wherein the modification counteracts the effect of the implantable electrode array 110 on mechanical properties of the cochlea. In an embodiment, the second gain is lower than the first gain and second frequency is higher than the first frequency.

In an embodiment, the speech processor is configured to access a conversion model 404/404' stored in a memory 402/402' to generate the modified acoustic stimulation signal 114', the modified acoustic stimulation signal 114' being configured to at least substantially counter the effect of the implantable electrode array 110 on mechanical properties of the cochlea of the patient. The memory 402 may be available within the hearing aid system such as within the speech processor unit (FIG. 3B, 302). Additionally or alternatively, the memory is a remote memory 402' separate from the speech processor unit (FIG. 3B, 302) and part of a remote device 408 such as a smartphone. The speech processor 104 may be communicatively coupled to the remote device 408 via a wireless link such a Bluetooth network 406.

In an embodiment, the conversion model 404/404' comprises a conversion function comprising at least one of an amplitude shift ΔL from the first gain L1 to the second gain L2 and a frequency shift Δf from the first frequency f1 to the second frequency f2 for at least substantially countering the effect of the implantable electrode array on mechanical properties of the cochlea of the patient.

In an embodiment, the conversion function is based on change in at least one of the first gain L1 and the first frequency f1 of the acoustic stimulation in the patient in response to at least one of characteristics of the implantable electrode array 110.

In an embodiment, the conversion function is based on an average change in at least one of the first gain L1 and the first frequency f1 of the acoustic stimulation in a sample population other than the patient in response to at least one of the characteristics of the implantable electrode array 110.

In an embodiment, the characteristics of the implantable electrode array 110 comprises one or a combination of a design of the implantable electrode array, mechanical properties of the implantable electrode array, insertion length of the implantable electrode array, distance of the implantable electrode array from the basilar membrane when the electrode array is located within the cochlea, and insertion technique for locating implantable electrode array into the cochlea.

In an embodiment, the conversion function is configured to be updated in accordance with variations in characteristics of the implantable electrode array 110 over time.

Figure 5:
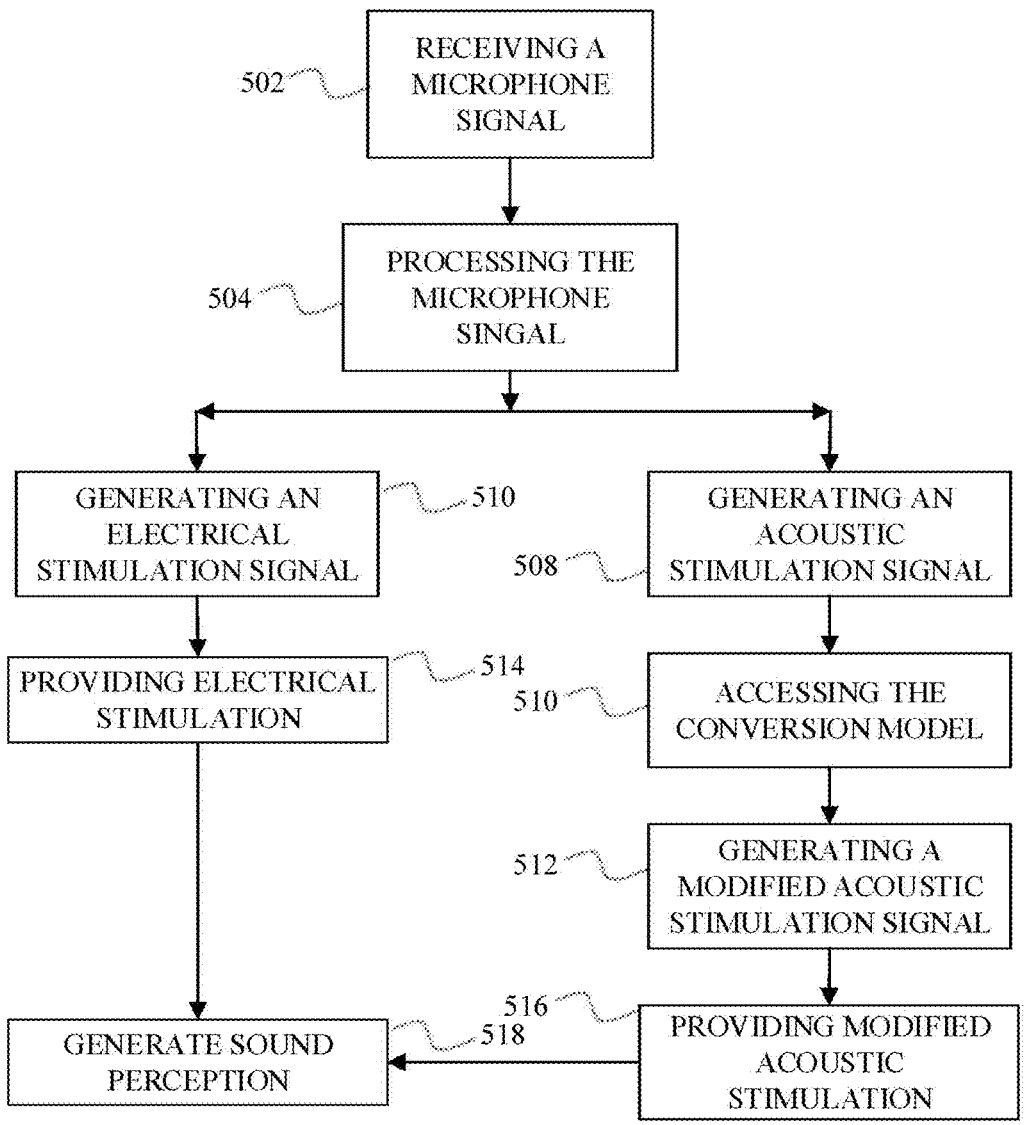
FIG. 5 illustrates a method for generating a sound perception using the dual stimulation hearing aid system according to an embodiment of the disclosure.

FIG. 5 illustrates a method for generating a sound perception using the dual stimulation hearing aid system according to an embodiment of the disclosure. The method for producing a dual-mode stimulation at a cochlea of the patient is disclosed. At 502, the method may include receiving at a microphone a sound and generating a corresponding microphone signal. At 504, the microphone signal received at the speech processor is processed and the speech processor is configured to produce an electrical stimulation signal at 510 and an acoustic stimulation signal at 508. The method may further includes at 510, the speech processor accessing the conversion model and utilizing the processing the acoustic stimulation signal in accordance with the conversion function. At 512, the speech processor generates a modified acoustic stimulation signal by modifying the acoustic stimulation signal at least for a part of a residual frequency range of a patient in dependence on effect of an implantable electrode array on mechanical properties of cochlea of the patient. Thereafter, at 514, the electrical stimulation based on the electrical stimulation signal to a cochlea within a non-residual frequency range of the patient and at 516, the modified acoustic stimulation based on the modified acoustic stimulation within the residual frequency range is provided to the cochlea of the patient using a first unit and a second unit respectively. Lastly, at 518 the modified acoustic stimulation and the electrical stimulation generates perception of sound to patient.

The first unit includes a cochlear implant communicatively coupled to the speech processor, wherein the cochlear implant comprising the implantable electrode array configured to be located within a cochlea of the patient. The second unit is communicatively connected to the speech processor. The second unit may be selected from a group consisting of an acoustic hearing aid configured to provide air conduction acoustic stimulation and a bone conduction hearing aid configured to provide a bone conduction acoustic stimulation.

Figure 6:
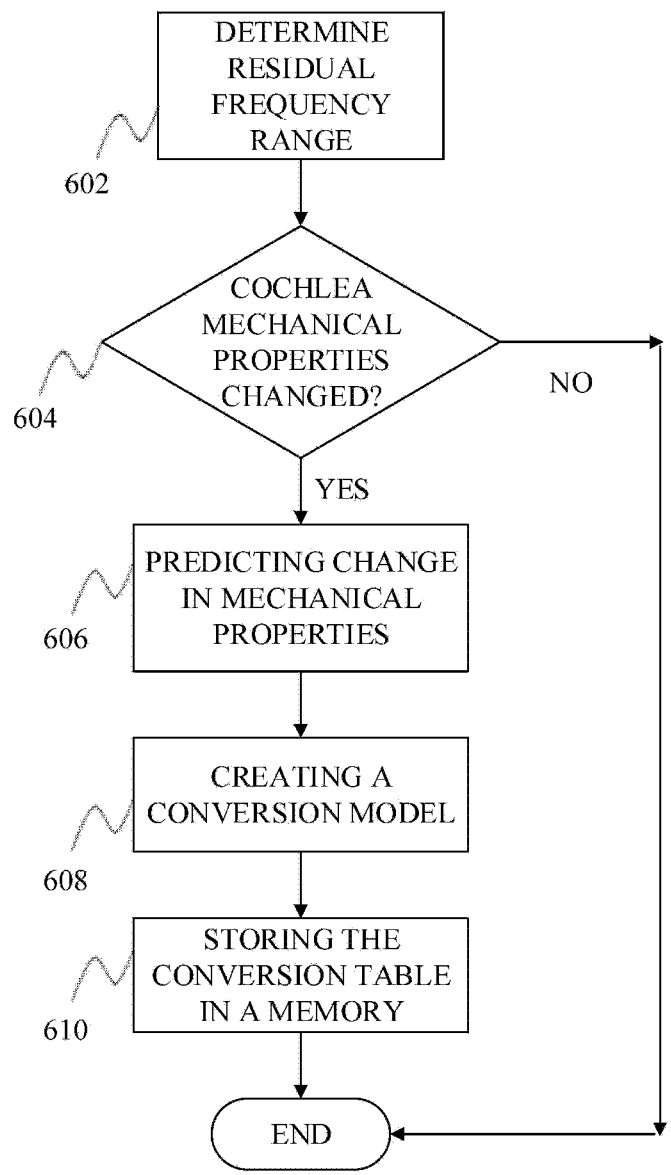
FIG. 6 illustrates a method for customizing a hearing aid system configured to produce an acoustic stimulation and an electrical stimulation according to an embodiment of the disclosure.

FIG. 6 illustrates a method for customizing a hearing aid system configured to produce an acoustic stimulation and an electrical stimulation according to an embodiment of the disclosure. The method includes at 602 determining a residual frequency range for a patient. At 604, a determination is made whether mechanical properties of a cochlea including basilar membrane of the patient is effected due to the presence of an implantable electrode array into the cochlea. If so, then at 606, the effect of the implantable electrode array on mechanical properties of cochlea of the patient is predicted; and at 608, a conversion model comprising a conversion function is created and at 610, the conversion model is stored in a memory that is accessible by a speech processor.

The conversion function comprises at least one of an amplitude shift from the a first gain to a second gain and a frequency shift from a first frequency to a second frequency for at least substantially countering the effect of the implantable electrode array on mechanical properties of the cochlea of the patient, the first gain and first frequency being based on an audiogram of the patient. Furthermore, the speech processor configured to process a received microphone signal for producing an electrical stimulation signal and an acoustic stimulation signal, the speech processor being further configured to generate a modified acoustic stimulation signal by modifying the acoustic stimulation signal at least for a part of a residual frequency range of the patient in dependence on effect of an implantable electrode array on mechanical properties of cochlea of the patient.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A hearing aid system comprising
a speech processor adapted to be communicatively coupled to a microphone and adapted to process a microphone signal received at the speech processor for producing an electrical stimulation signal and an acoustic stimulation signal, the speech processor being further configured to generate a modified acoustic stimulation signal by modifying the acoustic stimulation signal at least for a part of a residual frequency range of a patient in dependence on effect of an implantable electrode array on mechanical properties of cochlea of the patient, wherein the speech processor is adapted to generate the acoustic stimulation signal comprising a first gain corresponding to a first frequency comprised within the residual frequency range in accordance with an audiogram of the patient,
modify at least one of the first gain and the first frequency to generate the modified acoustic stimulation signal,
access a conversion model stored in a memory to generate the modified acoustic stimulation signal, the modified acoustic stimulation signal being configured to at least partially counter the effect of the implantable electrode array on mechanical properties of the cochlea of the patient, wherein the conversion model comprises a conversion function and the conversion function is based on a change in at least one of the first gain and the first frequency of the acoustic stimulation in a sample population other than the patient in response to at least one of characteristics of the implantable electrode array;

a first unit comprising a cochlear implant communicatively coupled to the speech processor, the cochlear implant comprising the implantable electrode array configured to be located within a cochlea of the patient and to provide an electrical stimulation based on the electrical stimulation signal to a cochlea within a non-residual frequency range of the patient; and a second unit communicatively coupled to the speech processor and adapted to provide a modified acoustic stimulation based on the modified acoustic stimulation signal to the cochlea within the at least in the part of the residual frequency range.

2. The hearing aid system according to claim 1, wherein the second unit is selected from a group consisting of an acoustic hearing aid configured to provide an air conduction acoustic simulation and a bone conduction hearing aid configured to provide a bone conduction acoustic stimulation.

3. The hearing aid system according to claim 2, wherein the effect of the electrode array on mechanical properties of cochlea comprises change in integrity of fine structures in the cochlea due to presence of the electrode array in the cochlea, thereby affecting mechano-electric transduction characteristics of the cochlea at least in the part of the residual frequency range.

4. The hearing aid system according to claim 2, wherein the effect of the electrode array on mechanical properties of cochlea comprises an increase in stiffness of at least a part of basilar membrane of the cochlea due to presence of the electrode array in the cochlea.

5. The hearing aid system according to claim 1, wherein the effect of the electrode array on mechanical properties of cochlea comprises change in integrity of fine structures in the cochlea due to presence of the electrode array in the cochlea, thereby affecting mechano-electric transduction characteristics of the cochlea at least in the part of the residual frequency range.

6. The hearing aid system according to claim 5, wherein the second gain is higher than the first gain and/or the second frequency is lower than the first frequency.

7. The hearing aid system according to claim 1, wherein the effect of the electrode array on mechanical properties of cochlea comprises an increase in stiffness of at least a part of basilar membrane of the cochlea due to presence of the electrode array in the cochlea.

8. The hearing aid system according to claim 1, wherein the speech processor is configured to
modify at least one of the first gain and the first frequency to generate the modified acoustic stimulation signal comprising at least one of a second gain at the first frequency, the first gain at a second frequency and the second gain at the second frequency, wherein the modification counteracts the effect of the implantable electrode array on mechanical properties of the cochlea.

9. The hearing aid system according to claim 1, wherein the conversion model comprises a conversion function comprising at least one of an amplitude shift from the first gain to the second gain and a frequency shift from the first frequency to the second frequency for at least partially countering the effect of the implantable electrode array on mechanical properties of the cochlea of the patient.

10. The hearing aid according to claim 1, wherein the conversion function is based on change in at least one of the first gain and the first frequency of the acoustic stimulation in the patient in response to at least one of characteristics of the implantable electrode array.

11. The hearing aid system according to claim 1, wherein the conversion function is based on an average change in at least one of the first gain and the first frequency of the acoustic stimulation in the sample population other than the patient in response to the at least one of the characteristics of the implantable electrode array.

12. The hearing aid according to claim 1, wherein the characteristics of the implantable electrode array comprises one or a combination of a design of the implantable electrode array, mechanical properties of the implantable electrode array, insertion length of the implantable electrode array, distance of the implantable electrode array from a basilar membrane when the electrode array is located within the cochlea, and insertion technique for locating implantable electrode array into the cochlea.

13. The hearing aid according to claim 1, wherein the conversion function is based on variation in audiometric data for the patient prior to insertion of the cochlear array and after the insertion of the cochlear array within at least in the part of the residual frequency range.

14. The hearing aid system according to claim 1, wherein the conversion function is configured to be updated in accordance with variations in characteristics of the implantable electrode array over time.

15. A method for producing a dual-mode stimulation at a cochlea of a patient
processing, at a speech processor communicatively coupled to a microphone, a microphone signal received at the speech processor for producing an electrical stimulation signal and an acoustic stimulation signal, the acoustic stimulation signal comprising a first gain corresponding to a first frequency comprised within the residual frequency range in accordance with an audiogram of the patient;

generating, at the speech processor, a modified acoustic stimulation signal by modifying the acoustic stimulation signal at least for a part of a residual frequency range of a patient in dependence on effect of an implantable electrode array on mechanical properties of cochlea of the patient, the modified acoustic stimulation signal being generated by modifying at least one of the first gain and the first frequency;

providing an electrical stimulation based on the electrical stimulation signal to a cochlea within a non-residual frequency range of the patient using a first unit comprising a cochlear implant communicatively coupled to the speech processor, the cochlear implant comprising the implantable electrode array configured to be located within a cochlea of the patient;

providing a modified acoustic stimulation based on the modified acoustic stimulation signal to the cochlea within the at least in the part of the residual frequency range using a second unit communicatively coupled to the speech processor; and accessing a conversion model stored in a memory to generate the modified acoustic stimulation signal, the modified acoustic stimulation signal being configured to at least partially counter the effect of the implantable electrode array on mechanical properties of the cochlea of the patient, wherein the conversion model comprises a conversion function and the conversion function is based on a change in at least one of the first gain and the first frequency of the acoustic stimulation in a sample population other than the patient in response to at least one of characteristics of the implantable electrode array.

16. The method according to claim 1, wherein modifying the acoustic stimulation signal is based on a conversion model comprising a conversion function that includes at least one of an amplitude shift from a first gain to a second gain and a frequency shift from a first frequency to a second frequency for at least partially countering the effect of the implantable electrode array on mechanical properties of the cochlea of the patient.

17. A non-transitory computer readable medium for storing a computer readable instructions which when executed causes the speech processor that is communicatively coupled to a microphone to
   process a microphone signal received at the speech processor for producing an electrical stimulation signal and an acoustic stimulation signal, the acoustic stimulation signal comprising a first gain corresponding to a first frequency comprised within the residual frequency range in accordance with an audiogram of the patient;
   generate a modified acoustic stimulation signal by modifying the acoustic stimulation signal at least for a part of a residual frequency range of a patient in dependence on effect of an implantable electrode array on mechanical properties of cochlea of the patient;
   provide an electrical stimulation based on the electrical stimulation signal to a cochlea within a non-residual frequency range of the patient using a first unit comprising a cochlear implant communicatively coupled to the speech processor, the cochlear implant comprising the implantable electrode array configured to be located within a cochlea of the patient;
   provide a modified acoustic stimulation based on the modified acoustic stimulation signal to the cochlea within the at least in the part of the residual frequency range using a second unit communicatively coupled to the speech processor, the modified acoustic stimulation signal being generated by modifying at least one of the first gain and the first frequency; and
   access a conversion model stored in a memory to generate the modified acoustic stimulation signal, the modified acoustic stimulation signal being configured to at least partially counter the effect of the implantable electrode array on mechanical properties of the cochlea of the patient,
   wherein the conversion model comprises a conversion function and the conversion function is based on a change in at least one of the first gain and the first frequency of the acoustic stimulation in a sample population other than the patient in response to at least one of characteristics of the implantable electrode array.

* * * * *